United States Patent
Leuck et al.

(10) Patent No.: US 7,329,515 B2
(45) Date of Patent: Feb. 12, 2008

(54) SOLID SUPPORT FOR THE SYNTHESIS OF 3'-AMINO OLIGONUCLEOTIDES

(75) Inventors: Michael Leuck, Hamburg (DE); Andreas Wolter, Hamburg (DE)

(73) Assignee: Sigma-Aldrich Co., St. Louis, MO (US)

( * ) Notice: Subject to any disclaimer, the term of this patent is extended or adjusted under 35 U.S.C. 154(b) by 538 days.

(21) Appl. No.: 10/830,484

(22) Filed: Apr. 21, 2004

(65) Prior Publication Data

US 2004/0220397 A1  Nov. 4, 2004

Related U.S. Application Data

(60) Provisional application No. 60/464,269, filed on Apr. 21, 2003.

(51) Int. Cl.
*C12P 19/34* (2006.01)
*C07H 21/02* (2006.01)
*C07H 21/04* (2006.01)
*C07C 229/56* (2006.01)

(52) U.S. Cl. .................. 435/91.5; 536/25.3; 536/25.31; 560/19

(58) Field of Classification Search ............... 435/91.5; 536/25.3, 25.31; 560/19
See application file for complete search history.

(56) References Cited

U.S. PATENT DOCUMENTS

| | | | |
|---|---|---|---|
| 5,141,813 | A | 8/1992 | Nelson |
| 5,419,966 | A | 5/1995 | Reed et al. |
| 5,942,610 | A | 8/1999 | Nelson et al. |

OTHER PUBLICATIONS

Dreef-Tromp et al. "A New Protected Acyl Protecting Group for Exocyclic Amino Functions of Nucleobases" (Tetrahedron Letters (1990) vol. 31, No. 3, pp. 427-430.*

Seneci, Solid Phase Synthesis and Combinatorial Technologies, (2000) Published by Wiley-Interscience, pp. 57-60.*
Asseline and Nguyen (1990) Tetrahedron Letters 31:81-84.
Avino et al. (1996) Bioorganic & Medicinal Chemistry 4(10):1649-1658.
Gamper et al. (1993) Nucleic Acids Research 21(1):145-150.
Lyttle et al. (1997) Bioconjugate Chem. 8:193-198.
Nelson et al. (1989) Nucleic Acids Research 17(18):7187-7194.
Petrie et al. (1992) Bioconjugate Chem. 3:85-87.
Vu et al. (1995) Bioconjugate Chem. 6:599-607.

* cited by examiner

*Primary Examiner*—Shaojia Anna Jiang
*Assistant Examiner*—Eric S Olson
(74) *Attorney, Agent, or Firm*—Polsinelli Shalton Flanigan Suelthaus PC

(57) ABSTRACT

The present invention discloses novel methods and solid supports for the synthesis of 3'-amino oligonucleotides. The novel supports are based on an unsubstituted or ring-substituted hydroxymethylbenzoyl linker element wherein the hydroxymethyl group is esterified to a solid phase bound carboxylic acid and the carbonyl group is linked to an amino alcohol as an amide. Oligonucleotides are conveniently synthesized on the novel supports with no modifications in the standard phosphoramidite synthesis scheme. The ester function of the support is cleaved under the alkaline deprotection conditions for oligonucleotides to provide a free hydroxymethyl group that aids in the release of the 3'-amino oligonucleotide products with a free amino group through neighbor group participation. The free amino group of the oligonucleotides is available for further conjugation reactions to haptens, reporter groups, surfaces or other small molecules or biomolecules. The methods provided are particularly mild, do not require any modifications in standard protocols for the synthesis and deprotection of oligonucleotides, provide the 3'-amino oligonucleotides free of side products and do not introduce chiral centers to the oligonucleotides.

28 Claims, 4 Drawing Sheets

SOLID SUPPORT FOR THE SYNTHESIS OF 3'-AMINO OLIGONUCLEOTIDES

FIELD OF INVENTION

Figure 1:
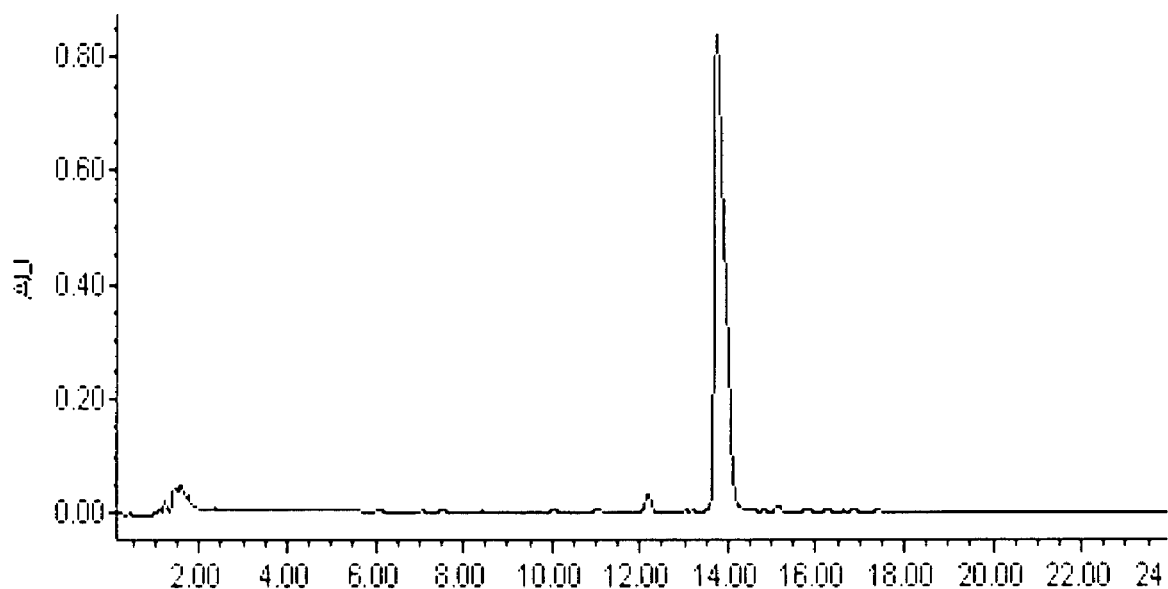

The present invention relates to the field of nucleotide chemistry. More specifically, the invention relates to the field of oligonucleotide synthesis including the chemical modification of oligonucleotides.

BACKGROUND OF THE INVENTION

The enormous increase in the demand for synthetic oligonucleotides fueled by the advances in DNA technology over the last few decades has been accelerated by recent progress in sequencing and decoding whole genomes, particularly the human genome. A number of methods in molecular biology and DNA-based diagnostics to amplify, detect, analyze and quantify nucleic acids are dependent on chemically synthesized oligonucleotides which are employed as primers and probes to amplify or to detect nucleic acid targets. Synthetic nucleic acids are also employed in therapeutic applications to block the expression of specific genes in a sequence dependent manner or to stimulate the immune system and present a very promising class of highly specific novel therapeutic agents which have the potential to be designed based on their sequence.

The properties of synthetic oligonucleotides can be manipulated and fine-tuned to the demands of their particular application by chemically conjugating the oligonucleotides to a variety of modifiers. Examples of modifiers include reporter groups to allow the facile detection of the modified oligonucleotides, e.g. fluorescent dyes, haptens to facilitate the specific capture and detection of oligonucleotides and their reaction products in diagnostic assays, e.g. biotin or digoxigenin, lipophilic modifiers to enhance the uptake of oligonucleotides in cells, e.g. cholesterol, modifiers to increase the biocompatibility and to reduce the exonucleolytic degradation of oligonucleotides, e.g. polyethylene or other groups which block the terminal hydroxyl groups, affinity modifiers to increase the affinity of oligonucleotides to complementary sequences, e.g. intercalators or nucleic acid groove binders, and peptides to achieve a variety of specific effects including targeted delivery to specific cell lines in an organism.

The development of efficient methods for the chemical synthesis of oligonucleotides and their conjugates over the past two decades has facilitated the routine provision of oligonucleotides of defined sequence and modifications. The current state of the art in oligonucleotide synthesis is automated solid phase synthesis using phosphoramidite chemistry, which in particular is based on the developments of McBride et al. (1983) Tetrahedron Letters 24:245-248 and Sinha et al. (1983) Tetrahedron Letters 24:5843-5846. These methods, together with related methods such as the hydrogen-phosphonate chemistry, have been extensively reviewed by Beaucage et al. (1992) Tetrahedron 48:2223-2311. Each of these references is specifically incorporated herein by reference in its entirety. The conjugation of oligonucleotides can be achieved through the incorporation of reagents in the solid phase synthesis which either introduce a functional group to the oligonucleotides for further selective manipulations or which directly introduce the desired modification in the course of the solid phase synthesis, as reviewed by Grimm et al. (2000) Nucleosides, Nucleotides & Nucleic Acids 19:1943-1965, and Beaucage et al. (1993) Tetrahedron 49:1925-1963, each of which is specifically incorporated herein by reference in its entirety.

The incorporation of modifications in synthetic oligonucleotides at their 3'-terminus has gained particular attention because a 3'-modification, in contrast to the more commonly applied 5'-modification, leaves the 5'-terminus of an oligonucleotide available for further synthetic or enzymatic modification and provides considerable stabilization against degradation in biological fluids. Unmodified nucleic acids are degraded in biological fluids, e.g. in cultured cells or whole organisms, by nucleases. 3'-Exonuclease activities contribute greatly to the observed instability. 3'-Terminal modifications provide significant stabilization against enzymatic degradation, as demonstrated e.g. for 3'-phosphopropyl amine oligonucleotides by Zendegui et al. (1992) Nucleic Acids. Res. 20:307-314, which is incorporated herein by reference in its entirety. 3'-Terminal modifications are therefore suitable to enhance the in-vivo stability of nucleic acids based therapeutics, such as antisense oligonucleotides, small interfering RNA, synthetic ribozymes and aptamers. The 3'-specific attachment of modifier groups, such as lipophilic groups, intercalating agents, reporter groups, polyethylene glycols, small peptides and other groups may further enhance the nucleolytic stability of oligonucleotides. These groups may also facilitate their penetration of cell membranes, increase their affinity to complementary target nucleic acids, or make them traceable in a biological system. An example of the application of 3'-amino modifications in the field of oligonucleotide based therapeutics is provided by Zerial et al. (1987) Nucleic Acids. Res. 15:9909-9919, which is incorporated herein by reference in its entirety.

The 3'-modification of oligonucleotides is particularly useful in the synthesis of bi-fluorescent probes which contain two different fluorescent dyes at their 3'- and 5'-termini. Bi-fluorescent probes are widely employed in oligonucleotide based diagnostic assays such as real-time quantitative PCR. Bi-fluorescent probes are also employed as molecular beacons; see Tyagi et al. (1996) Nat. Biotechnol. 14:303-308, hydrolysis probes (Taqman™ technology, Perkin-Elmer Applied Biosystems, Foster City, Calif., USA), see Heid et al. (1996) Genome Research 6:986-994, and scorpion probes, see Whitcombe et al. (1999) Nat. Biotechnol. 17:804-807, each of which is incorporated herein by reference in its entirety.

The incorporation of a primary amino group at the 3'-terminus of a synthetic oligonucleotide is of particular interest due to the high reactivity of primary amino groups which allows for the chemoselective derivatization of the corresponding oligonucleotides. 3'-Amino oligonucleotides can be conveniently conjugated to a variety of reporters, haptens or other modifiers by reacting the amino group in a selective manner with active ester derivatives of the moieties to be conjugated. Many active ester derivatives of such moieties are either commercially available or can be synthesized by standard esterification reactions. 3'-Amino oligonucleotides can also be covalently attached to surfaces with electrophilic groups, as described e.g. by Gerry et al. (1999) J. Mol. Biol. 292:251-262, which is incorporated herein by reference in its entirety.

3'-Amino oligonucleotides are conveniently prepared using solid phase synthetic methods on specialty solid supports. Such supports are applied in the same manner as conventional supports for the synthesis of unmodified oligonucleotides, but release oligomers with free 3'-amino groups during the standard deprotection of the oligonucleotides. A suitable support for the synthesis of 3'-amino derivatized oligonucleotides would ideally fulfill the following criteria:

A) it would be compatible with and stable under the standard phosphoramidite synthetic method for oligonucleotides;

B) it would comprise a linkage to the oligonucleotide that is cleaved during the deprotection of the nucleobases, wherein said cleavage does not require the introduction of reagents which are not commonly employed in the deprotection of oligonucleotides;

C) it would be cleavable from the oligonucleotide in a reaction time that is comparable to the time employed in standard deprotection conditions for the removal of base protective groups;

D) it would provide the 3'-amino oligonucleotide without side products derived from modifications of the amino group, e.g. acylations of the amine;

E) it would not generate diasteromeric mixtures of oligonucleotides due to the presence of chiral centers on the support; and F) it would be preparable in a simple and efficient manner.

Standard deprotection conditions are such conditions that are commonly employed to remove the base protective groups: isobutyryl from guanine residues and benzoyl from adenine and cytosine residues, e.g. an incubation of the support in concentrated aqueous ammonia at 55° C. for 8 hours.

Several reports on derivatized solid supports that are suitable for the synthesis of oligonucleotides with 3'-amino modifications have already appeared in the literature, but none of the described products meet all of the above criteria for a generally useful support. The known supports can be divided in two groups. The first group contains a protected amino group wherein the protective group is attached to the support and the 3'-amino oligonucleotide is released upon the cleavage of the protective group. The protective group for the amino function also serves as a linker in this group of supports, which connects the solid phase of the support with the oligonucleotide. The second group of supports contains a branched linker wherein the linker contains a protected amino group on a side arm and the oligonucleotide is attached to the solid phase of the support through another functionality of the linker. In this group of supports, the 3'-amino oligonucleotide is released upon cleavage of the linker from the support and the amino function is liberated either simultaneously or in a separate step through the removal of the side arm protective group.

An example out of the first group of supports for the synthesis of 3'-amino oligonucleotides has been described by Asseline et al. (1990) Tetrahedron Letters 31:81-84, which is incorporated herein by reference in its entirety. The linker of the support described by Asseline et al. contains a disulfide group, which is cleaved with dithiothreitol to release the 3'-amino oligonucleotide. Dithiothreitol is not commonly employed in the solid phase synthesis of oligonucleotides and its application is undesirable. Additionally, the described support is not easy to prepare and requires multiple synthetic steps in solution and on the support.

Other examples of the first group of solid supports have been described by Kumar et al. (1996) Bioorg. Med. Chem. Lett. 6:2247-2252, which is incorporated herein by reference in its entirety. The linkers employed in the supports described by Kumar et al. contain a sulfonylethyl group that is cleaved in concentrated aqueous ammonia at 55° C. to release the 3'-amino oligonucleotide products. The described incubation time in concentrated ammonia is 16 hours, which exceeds the standard deprotection time for oligonucleotides. Additionally, supports are prepared in multi-step processes and a variety of reagents are employed to manipulate the functional groups of the corresponding solid phase intermediates. Such reactions are difficult to monitor and the purity of the intermediates can not easily be demonstrated. The supports are therefore difficult to prepare and their use is not compatible with standard deprotection conditions and with base sensitive modifications of oligonucleotides.

In another example of the first group of supports Petrie et al. (1992) Bioconjugate Chem. 3:85-87, and Reed et al., U.S. Pat. No. 5,419,966, each of which is incorporated herein by reference in its entirety, describe the application of the phthaloyl protective group. The phthaloyl group is removed from the 3'-amine oligonucleotide with concentrated ammonia in 16 hours at 55° C. The required time for the removal of the phthaloyl protective group is longer than the standard deprotection time for oligonucleotides, which reduces the throughput in the synthesis of oligonucleotides and makes the support incompatible with base-sensitive modifications. A similar support is also disclosed by Lyttle et al. (1997) Bioconjugate Chem. 8:193-198, which is incorporated herein by reference in its entirety. Lyttle et al. describe a linker based on trimellitic acid that is cleavable from the 3'-amino oligonucleotide by treatment with concentrated ammonia at 55° C. for 18-24 hours. The applied reaction time for the cleavage of the support from the oligonucleotide is longer than the standard reaction time for the deprotection of nucleobases. In addition, 20-30% of a side product was observed in the synthesis of a 3'-amino 14-mer oligonucleotide, which was tentatively characterized as the 3'-amino oligonucleotide conjugated to trimellitic acid at the amino group, which indicates incomplete cleavage between the trimellitic acid linker and the oligonucleotide even under the prolonged time of reaction in ammonia.

In other variations of supports which utilize an amino protective group as part of the linker to the support Avino et al. (1996) Bioorg. Med. Chem. 4:1649-1658, which is incorporated herein by reference in its entirety, applied derivatized o-nitrophenylethyl-(o-NPE) and 9-fluorenylmethyloxycarbonyl (Fmoc) amino protective groups attached to the support through substituents at their aromatic rings. The linker based on the Fmoc-group was, however, believed not to be stable enough under the standard conditions of phosphoramidite mediated oligonucleotide synthesis as low yields of 3'-amino oligonucleotides were observed. In contrast, the o-NPE-group could not be cleaved completely with concentrated ammonia and the stronger base DBU had to be used as a 0.5 M solution in pyridine for 16 hours to achieve efficient cleavage. The application of a solution of DBU in pyridine is an additional step, which requires additional work-up steps and is therefore undesirable.

Examples of the application of a branched linker based on an 3-amino-1,2-propanediol linker unit are provided by Nelson et al. (1989) Nucleic Acids Res. 17:7187-7194, and U.S. Pat. No. 5,141,813, each of which is incorporated herein by reference in its entirety. The linker in the solid support of Nelson et al. utilizes the vicinal hydroxyl groups of 3-amino-propane-1,2-diol as attachment points for the oligonucleotide and the solid phase whereas the amino group of the linker is Fmoc protected. Oligonucleotide products synthesized on this support contain a 3'-amino-2-hydroxypropylphosphate moiety. The support has several disadvantages. The Fmoc protective group of the amino function is not completely stable to the conditions applied in a phosphoramidite mediated oligonucleotide synthesis and is partially removed in the process. The resulting free amino group is exposed to the capping reagent acetic anhydride during the oligonucleotide synthesis and the amino groups are therefore partially acetylated. The acetylated amino groups are stable during the deprotection of the nucleoside bases and the 3'-amino oligonucleotide is therefore contaminated with the corresponding 3'-acetylamino species. The utilization of vicinal diol groups also facilitates the cleavage of the 3-amino-2-hydroxypropylphosphate moiety from the oligonucleotide products through cyclic phosphate intermediates, resulting in unmodified 3'-OH oligonucleotides. 3'-acetylamino oligonucleotides and non-modified 3'-OH oligonucleotides were observed as contaminants in 3'-amino oligonucleotides prepared with the support of Nelson et al. e.g. by Vu et al. (1995) Bioconjugate Chem. 6:599-607, which is incorporated herein by reference in its entirety. Another disadvantage of solid supports based on the branched 3-amino-propane-1,2-diol element is the introduction of a chiral center to the 3'-amino oligonucleotide products. Oligonucleotides prepared on this support exist as mixtures of two diastereoisomers as a consequence of the undefined stereochemistry of the carbon atom at the linker branching point, i.e. the carbon atom in the 2-position of the 3-amino-propane-1,2-diol skeleton. The existence of oligonucleotide diastereoisomers complicates the analysis of the 3'-amino oligonucleotides, as well as, their subsequent application in the conjugation of reporter molecules or haptens.

Nelson et al. also describe a solid support based on the branched linker unit 2-(4-aminobutyl)-propane-1,3-diol (i.e. 6-amino-2-hydroxymethyl-hexan-1-ol), see Nelson et al., U.S. Pat. No. 5,942,610, which is incorporated herein by reference in its entirety. This solid support is an improved version of the support based on the 3-amino-1,2-propanediol linker unit. It overcomes some of the associated disadvantages, because it utilizes a 1,3-diol system for the attachment of the oligonucleotide and the solid phase to the linker in contrast to the vicinal 1,2-diol system that was employed in the prior support. The undesired formation of unmodified 3'-OH oligonucleotides through cyclic phosphate intermediates is effectively suppressed in this system. The support, nevertheless, still has the following major disadvantages. It carries an Fmoc group to protect the amino function on the branch of the linker, which as noted above is not completely stable to the conditions employed in the capping steps of a phosphoramidite mediated oligonucleotide synthesis resulting in the formation of amino-acetylated side products. It also introduces a chiral center to the 3'-amino oligonucleotides, i.e. the carbon atom in the 2-position of the propane-1,3-diol system. This leads to two diastereomeric oligonucleotide products in each 3'-amino oligonucleotide, which as also noted above complicates the analysis of the oligomer and the monitoring of subsequent applications of the 3'-amino oligonucleotides.

Solid supports that contain an amino function on a branched linker can be further derivatized by conjugating the amino function to small molecules, haptens or reporter groups. The synthesis of oligonucleotides on such derivatized supports results in the corresponding 3'-modified oligonucleotides after cleavage and deprotection, which alleviates the need to prepare the corresponding 3'-modified oligonucleotides by post synthetic conjugation methods from 3'-amino oligonucleotides. The utility of this approach has been demonstrated e.g. by Gamper et al. (1993) Nucleic Acids Res. 21:145-150, with a 5-hydroxymethyl-pyrrolidine-(3R-trans)-3-ol linker element in the synthesis of oligonucleotides conjugated to acridine and to cholesterol at their 3'-end, and by Stetsenko et al. (2001) Bioconjugate Chem. 12:576-586, with a homoserine based linker element in the synthesis of oligonucleotides conjugated to 4-iodophenyl acetic acid, 6-carboxyfluorescein, biotin and other small molecules at their 3'-end, and by Mullah et al. (1998) Nucleic Acids Res. 26:1026-1031, with a 2-amino-propane-1,3-diol linker element in the synthesis of 3'-TAMRA modified oligonucleotides. Each of these references is specifically incorporated herein by reference in its entirety. Although this approach is useful for targeting a particular conjugate, it is limited in that a specialty support must be prepared individually for every hapten or reporter to be conjugated. In contrast, sequences with free amino groups, once prepared on a standard support, can be aliquoted and conjugated to a variety of different small molecules, haptens or reporter groups, thus eliminating the need to conduct multiple oligonucleotide synthesis if the same sequence is desired with different 3'-modifications. Additionally, oligonucleotides with free amino groups can be stored and used at a later date for the conjugation of another molecule.

The method of using specialty derivatized supports for each modification is also limited to those modifications that are stable under the conditions of oligonucleotide synthesis and under the conditions of cleavage and deprotection of the oligonucleotides. Many desirable 3'-modifications do not fulfill the stability criterion and can not be prepared with such solid supports. Other modifications require non-standard treatments or specialty reagents in the assembly of the oligonucleotide chain or in the cleavage and deprotection of the oligonucleotides as exemplified in the preparation of 3'-TAMRA modified oligonucleotides described by Mullah et al., wherein a mixture of tert-butylamine, methanol and water in a ratio of 1:1:2, v/v, is used to cleave and deprotect the conjugated oligonucleotide. Non-standard reagents are highly undesirable in routine schemes for the preparation of oligonucleotides, because modified and unmodified oligonucleotides are typically prepared in the same synthesis facilities by the same personnel and should be fully compatible with each other in order to obtain economic viability and to reduce the probability of errors resulting from the use of different reagents for different sets of oligonucleotides.

Although, as exemplified above, a variety of solid supports for the synthesis of 3'-amino oligonucleotides has been described, and some of the described solid supports are commercially available, there is no known solid support that combines all of the desired favorable features of such a support described in the criteria A) to F) above. The known supports either require extended cleavage and deprotection times, or inherently result in side products such as acetylated derivatives of the 3'-amino oligonucleotides, or result in diastereomeric mixtures of 3'-amino oligonucleotide products, or suffer from a combination of these disadvantages.

The present invention discloses novel methods and solid supports for the synthesis of 3'-amino oligonucleotides wherein the cleavage of the oligonucleotides from the support and the removal of their base protective groups can be conducted under mild alkaline conditions and wherein the 3'-amino oligonucleotides are obtained as single diastereoisomers free from side products. The novel solid supports described herein contain an ortho-hydroxymethyl benzoyl protective group (HMB-group) for the amino function wherein the hydroxymethyl group is employed for the attachment of the protective group to the solid phase of the support and the carbonyl group of the benzoyl moiety serves as the conjugation point for the amino-oligonucleotide. The HMB-group may optionally contain additional substituents in the aromatic ring.

SUMMARY OF THE INVENTION

The present invention discloses novel methods and solid supports for the synthesis of 3'-amino oligonucleotides wherein the cleavage of the oligonucleotides from the support and the removal of their base protective groups can be conducted under mild alkaline conditions and wherein the 3'-amino oligonucleotides are obtained as single diastereoisomers free from side products. The novel solid supports of this invention contain a ortho-hydroxymethyl benzoyl protective group (HMB-group) for the amino function wherein the hydroxymethyl group is employed for the attachment of the protective group to the solid phase of the support and the carbonyl group of the benzoyl moiety serves as the conjugation point for the amino-oligonucleotide. The HMB-group may optionally contain additional substituents in the aromatic ring.

The novel solid supports of the invention are illustrated by formula (2) below:

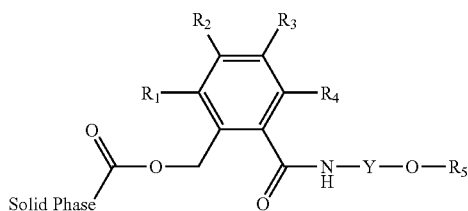

2 wherein $R_1$, $R_2$, $R_3$ and $R_4$ are independently selected from the group consisting of H, alkyl with up to 4 carbon atoms, heteroalkyl with up to 4 carbon atoms, phenyl, alkoxy with up to 4 carbon atoms, heteroalkoxy with up to 4 carbon atoms, carboxy, alkyloxycarbonyl with up to 4 carbon atoms in the alkyl chain, alkylcarbamoyl with up to 4 carbon atoms in the alkyl chain, halo, cyano, nitro, sulfo and alkylsulfonyl with up to 4 carbon atoms in the alkyl chain;

$R_5$ is H or a protective group that is removed in the first deblocking step of a solid phase oligonucleotide synthesis; and Y is an organic spacer group comprising a straight or branched chain of one or more methylene groups, wherein the chain is optionally interrupted by one or more moieties independently selected from the group consisting of oxygen atoms, carbonyl groups, amide groups, ureido groups, urethane and aryl groups.

The novel methods and supports described herein fulfill the criteria of compatibility with the standard phosphoramidite synthetic method for oligonucleotides. Additionally, the novel methods and supports described herein do not generate diasteromeric mixtures of oligonucleotides, as the corresponding supports do not introduce chiral centers to the oligonucleotides.

The novel supports described herein comprise a linkage to the oligonucleotide that is cleaved during the deprotection of the nucleobases, wherein the cleavage does not require the introduction of reagents which are not commonly employed in the deprotection of oligonucleotides, they are cleavable from the oligonucleotide in a reaction time that is comparable to the time employed in standard deprotection conditions for the removal of base protective groups, they provide the 3'-amino oligonucleotide without side products derived from modifications of the amino group, e.g. acylations of the amine, and they are preparable in a simple and efficient manner.

The novel methods are compatible with various base protection schemes for the synthesis of oligonucleotides including the protection of guanine bases with the N,N-dimethylformamidine protective group.

BRIEF DESCRIPTIONS OF THE DRAWINGS

FIG. 1 illustrates the analysis of the oligonucleotide 3'-amino-d($T_{10}$) (27) (SEQ ID NO:1) by anion exchange chromatography after its synthesis on solid support (25) and cleavage/deprotection in concentrated aqueous ammonia as described in Example 3.

Figure 2A:
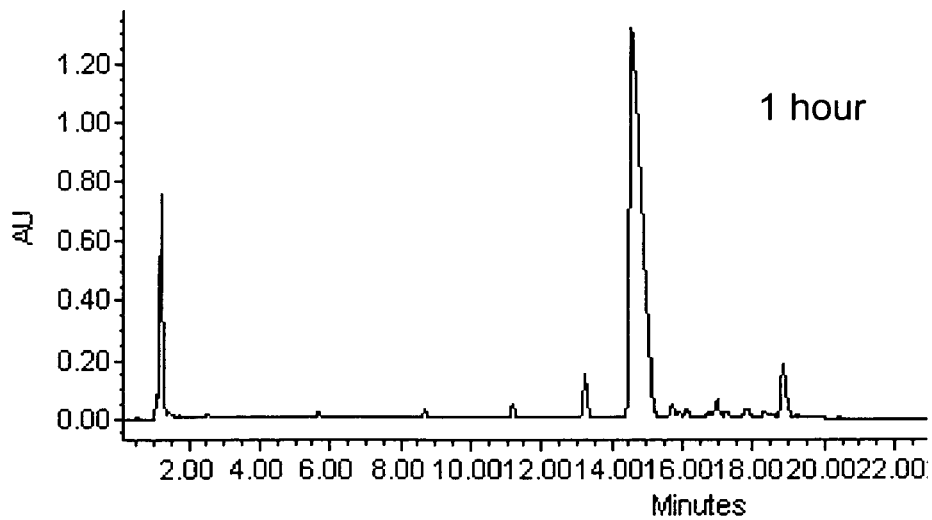
Figure 2B:
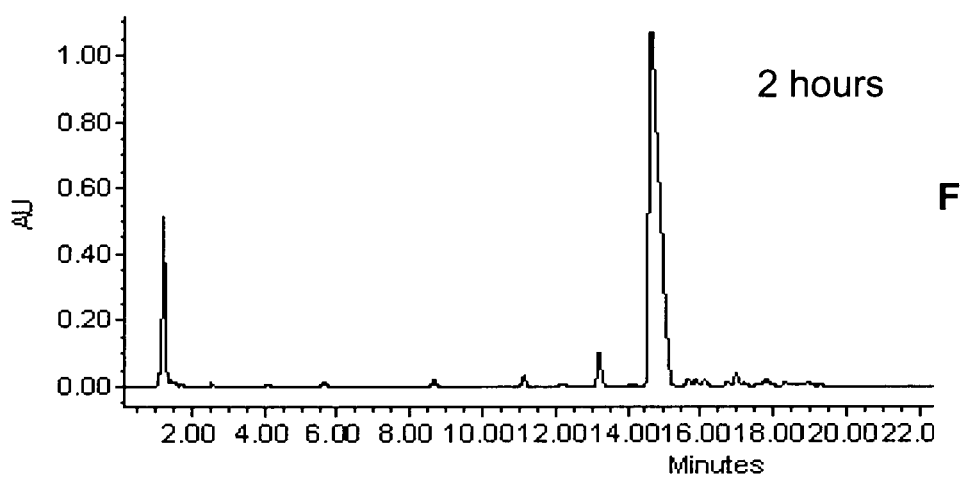
Figure 2C:
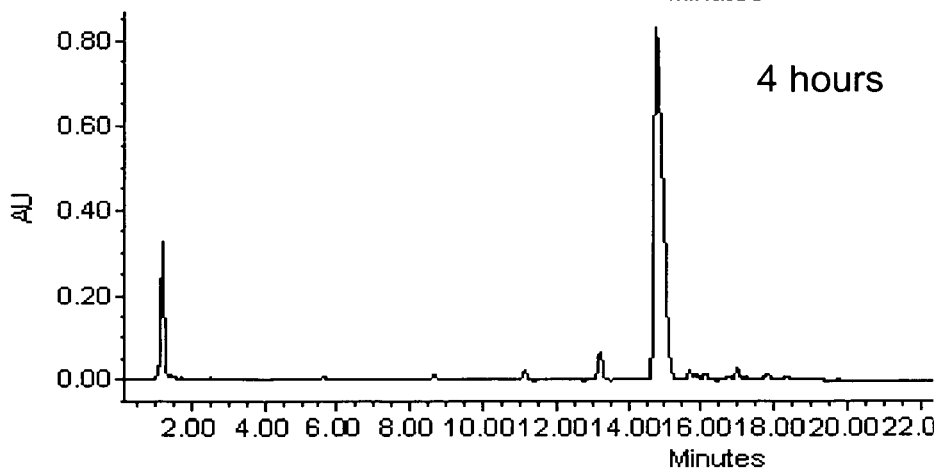

FIGS. 2A-C illustrate the analysis of the oligonucleotide 3'-amino-d($T_{10}$) (27) by anion exchange chromatography after its synthesis on solid support (26) and cleavage/deprotection in concentrated aqueous ammonia at 55° C. with varying incubation times in ammonia as described in Example 6.

Figure 3:
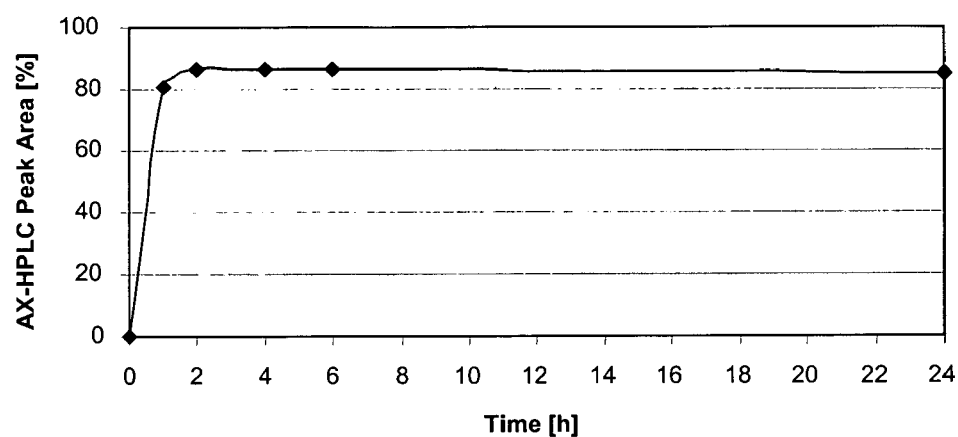

FIG. 3 displays the observed yield of the oligonucleotide 3'-amino-d($T_{10}$) (27) as determined by anion exchange chromatography after its synthesis on solid support (26) and cleavage/deprotection in concentrated ammonia at 55° C. in relation to the applied incubation time in concentrated ammonia as described in Example 6.

Figure 4:
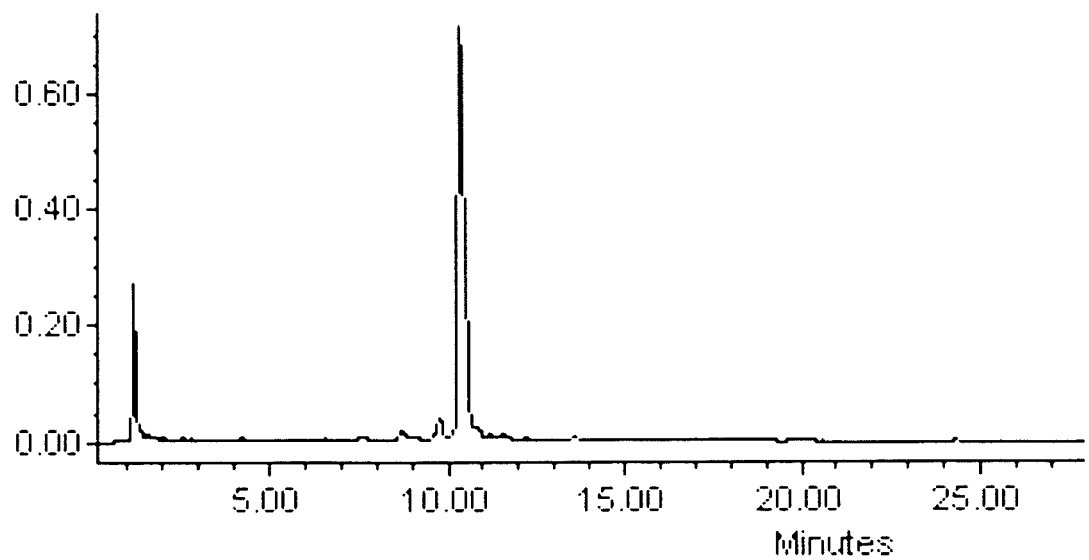

FIG. 4 illustrates the analysis of the oligonucleotide 3'-amino-5'-d(CTC-TCA-GCG-AGC-CTC-AA) (28) (SEQ ID NO:2) by anion exchange chromatography after its synthesis on solid support (26) and cleavage/deprotection in concentrated ammonia as described in Example 7.

Figure 5:
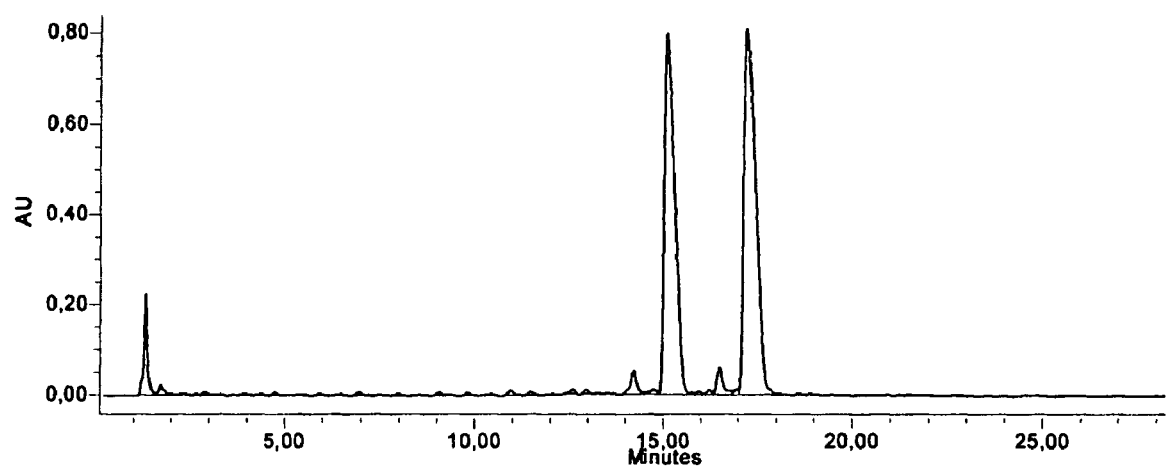

FIG. 5 displays the anion exchange chromatogram of the oligonucleotide products 3'-amino-d($T_{14}$) (SEQ ID NO:3) and d($T_{15}$) (SEQ ID NO:4) that were prepared on a mixture of a thymidine loaded CPG support and solid support (26) in the same synthesis column when the sequence d($T_{15}$) was programmed into the synthesis instrument, as described in Example 8.

DETAILED DESCRIPTION OF THE INVENTION

Various terms are used herein to refer to aspects of the present invention. To aid in the clarification of the description of the components of the invention, the following descriptions are provided.

It is to be noted that the term "a" or "an" entity refers to one or more of that entity; for example, an oligonucleotide refers to one or more oligonucleotides. As such, the terms "a" or "an", "one or more" and "at least one" are used interchangeably herein.

The term "oligonucleotide synthesis" as used herein refers to solid phase oligonucleotide synthesis (SPOS) using either phosphoramidite, phosphotriester and/or nucleoside hydrogen phosphonate chemistries known to those skilled in the art and described e.g. by Gait, ed., "Oligonucleotide synthesis: A practical approach," (1984) IRL Press, Oxford, UK; Eckstein, ed., "Oligonucleotides and analogs: A practical approach," (1991) IRL Press, Oxford, UK; Beaucage et al. (1992) Tetrahedron 48:2223-2311; McBride et al. (1983) Tetrahedron Lett. 24:245-248 and Sinha et al.(1983) Tetrahedron Lett. 24:5843-5846, each of which is specifically incorporated herein by reference in its entirety, or any other chemistry used in solid phase oligonucleotide synthesis. Typically, oligonucleotide synthesis involves a number of chemical steps that are performed in a cyclical repetitive manner throughout the synthesis, each cycle adding one nucleotide synthon to the growing oligonucleotide chain. The chemical steps involved in a cycle are a deprotection step that liberates a functional group for further chain elongation, a coupling step that incorporates a nucleotide synthon into the oligonucleotide to be synthesized, and other steps as required by the particular chemistry used in the oligonucleotide synthesis, e.g. an oxidation step required with the phosphoramidite chemistry. Optionally, a capping step that blocks those functional groups which were not elongated in the coupling step is inserted in the cycle. The extension of the oligonucleotide chain in the course of an oligonucleotide synthesis is typically pursued in the 3' to 5' direction by adding nucleotide synthons carrying a suitable protective group at the 5'-position, e.g. the widely employed DMT-group (DMT=dimethoxytrityl=bis(4-methoxyphenyl) phenylmethyl), and a suitable activatable group, e.g. a phosphoramidite group, at the 3'-position to form a linkage to the 5'-position of the growing chain. The extension of the oligonucleotide chain may alternatively be pursued in the 5' to 3' direction by adding nucleotide synthons in the coupling reaction that carry suitable protective groups at the 3'-position, e.g. a DMT-group, and a suitable activatable group, e.g. a phosphoramidite group, at the 5'-position to form a linkage to the 3'-position of the growing chain. This approach is exemplified in the synthesis of oligodeoxynucleotides with 3'-DMT protected deoxynucleoside 5'-phosphoramidites, as described by e.g. Robles et al. (1995) Nucleic Acids Res. 23:4151-4161, which is specifically incorporated herein by reference in its entirety, or in the synthesis of N3'-P5' phosphoramidite oligonucleotides with N3'-trityl protected nucleoside 5'-phosphoramidites, as described e.g. by Fearon et al. (1998) Nucleic Acids Res. 26:3813-3824, which is specifically incorporated herein by reference in its entirety. Nucleotide synthons that are applied in the coupling step of an oligonucleotide synthesis cycle typically are mononucleotide synthons, e.g. the commercially available 5'-DMT protected deoxynucleoside 3'-phosphoramidites, but may be dinucleotide synthons, as described by Kumar et al. (1984) J. Org. Chem. 49:4905-4912, which is incorporated herein by reference in its entirety, or trinucleotide synthons, as described by Ono et al. (1995) Nucleic Acids Res. 23:4677-82, which is incorporated herein by reference in its entirety, or synthons that consist of more than 3 nucleotide units.

As used herein the term "oligonucleotide" refers to a single stranded chain of either deoxyribonucleotides or ribonucleotides or chemical modifications thereof, such as e.g. nucleotides with a O2'-C4'-methylene bridge in their sugar portion, which are the constituting nucleotides of locked nucleic acids (LNA). Modifications include, but are not limited to, those that provide other chemical groups that incorporate additional charge, polarizability, hydrogen bonding, electrostatic interaction, and functionality to the individual nucleotides or their corresponding bases or to the oligonucleotides as a whole. Such modifications include, but are not limited to, modified bases such as 2'-position sugar modifications, e.g. O2'-methyl- or 2'-fluoro modifications, 5-position pyrimidine modifications, 8-position purine modifications, modifications at the exocyclic amino group of cytosine, incorporation of 5-bromo-uracil; backbone modifications, methylations, bases that can be part of unusual base-pairing combinations such as the isobases isocytidine and isoguanidine and the like. Modifications further include attached labels and reporter molecules, such as fluorescent dyes, biotin, minor groove binders and the like that are known to those skilled in the art. In addition modifications include modified backbones of the oligonucleotides, examples being peptide nucleic acids (PNA), phosphorothioate DNA, methylphosphonate DNA and other modifications known to those skilled in the art and reviewed by Micklefield (2001) Current Medicinal Chemistry 8:1157-1179, which is incorporated herein by reference in its entirety. Oligonucleotides, as referred to in this invention can consist of any combinations of the nucleotides and their modifications described above and can have either a few, e.g. up to 20, or many, e.g. 20 to several hundred or more, nucleotides incorporated in their chain, the total number of nucleotides being denoted n in the context of this invention.

As used herein the term "3'-amino oligonucleotide" refers to an oligonucleotide as defined above that comprises an amino group at its 3'-terminus. The amino group is covalently attached to the 3'-terminal nucleotide of the oligonucleotide via a spacer. The spacer preferably consists of an alkylidene group of the formula —(CH$_2$)$_n$— or —CH$_2$CH$_2$—(OCH$_2$CH$_2$)$_n$—

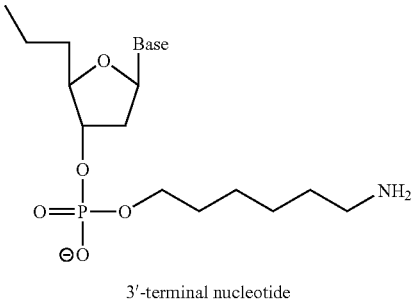

3'-terminal nucleotide with n ranging from 1 to 10, or an alkyl-substituted derivative thereof wherein each alkyl substituent substitutes for one of the hydrogen atoms and contains up to 4 carbon atoms, or a hetero-substituted derivative thereof wherein one or more of the CH$_2$-groups are substituted by oxygen, and a phosphate group that is attached to the 3'-terminal nucleotide of the oligonucleotide. The attachment of the amino group to the oligonucleotide is illustrated for example by formula (1), wherein the spacer is —(CH$_2$)$_6$— and the phosphate group is linked to the oligonucleotide at the 3'-OH group of its 3'-terminal nucleotide.

As used herein the term "base protective group" refers to a protective group useful in oligonucleotide synthesis for protecting exocyclic amino functions of nucleobases or chemical modifications thereof, as exemplified by the protective groups including, but not limited to the benzoyl protective group for adenine and cytosine, the isobutyryl protective group for guanine, tert-butylphenoxyacetyl protective groups for adenine, cytosine and guanine, N,N-dimethylformamidine protective groups for adenine, cytosine and guanine and any other protective groups for nucleobases including any chemical modification thereof, known to those skilled in the art.

As used herein the term "standard deprotection conditions" refers to conditions for the cleavage and deprotection of an oligonucleotide prepared by a solid phase oligonucleotide synthesis that are applied by those skilled of the art to simultaneously remove benzoyl protective groups from the exocyclic amino groups of adenine and cytidine nucleobases and isobutyryl protective groups from the exocyclic amino group of guanine nucleobases. Examples of standard deprotection conditions include, but are not limited to the incubation of the corresponding oligonucleotides in concentrated aqueous ammonia at 55° C. for 8 hours and the application of gaseous ammonia under a pressure of 10 bar at 25° C. for 7 hours, as described by Boal et al. (1996) Nucleic Acids Res. 24:3115-3117, which is incorporated herein by reference in its entirety. It is known to those skilled in the art that variations of the deprotection time can be applied with a concomitant variation of the temperature when taking into account that the deprotection rate is accelerated by a factor of approximately 2 if the temperature is raised by 10° C. For example, the deprotection with concentrated aqueous ammonia can also be conducted in 4 hours at 65° C. or in 2 hours at 75° C. Such variations are also considered standard deprotection conditions herein.

The term "solid phase" as used herein refers to a polymer, which is insoluble in the medium employed in a particular reaction or unit operation performed to synthesize or purify oligonucleotides. A solid phase can be an inorganic polymer including, but not limited to inorganic oxides such as silica, alumina, zeolites and controlled pore glass (CPG), a modified inorganic polymer, such as silica or CPG with an organic coating, e.g. aminopropyl-silane derivatized silica or CPG, or an organic polymer including, but not limited to polystyrene, polyacrylamide, polymethacrylate, polyvinylalcohol, or other synthetic polymers, carbohydrates such as cellulose and starch or other polymeric carbohydrates, or other organic polymers and any copolymers, composite materials or combination of the above inorganic or organic materials. Solid phases, as defined herein, may comprise functional groups, such as hydroxyl-, carboxyl- or amino-groups or other functional groups known to those skilled in the art, which may or may not be protected.

The term "solid support" as used herein refers to a solid phase that is derivatized to comprise functional groups which are suitable to participate in the coupling reaction of an oligonucleotide synthesis. The functional groups are either unprotected, e.g. free hydroxyl groups, or protected, e.g. DMT-protected hydroxyl groups, that need to be deprotected prior to the coupling reaction. A solid support is subjected to cycles of deprotection reactions, coupling reactions with nucleotide synthons, such as e.g. phosphoramidite synthons, and eventually other chemical reactions in a stepwise manner to build oligonucleotides on the surface of the solid phase, as described under the term "oligonucleotide synthesis" and in the references cited therein.

The term "electron withdrawing substituent" as used herein refers to a monovalent group or moiety of a molecule that draws electrons to itself more than a hydrogen atom would if it occupied the same position in the molecule. An electron withdrawing substituent is also referenced as a substituent with a -I effect. The concept of electron withdrawing substituents as used herein is the same as explained in standard chemical text books known to those skilled in the art, e.g. in J. March, *Advanced Organic Chemistry*, A Wiley-Interscience Publication, 1985, pp 16-18, which is incorporated herein by reference. Groups or moieties that are generally considered as being electron withdrawing include, but are not limited to nitro, fluoro, chloro, bromo, cyano, alkylsulfonyl, alkylcarbonyl, alkoxycarbonyl, trialkylammonium and any other groups known to those skilled in the art that exert a -I effect.

The present invention discloses novel methods and solid supports for the synthesis of 3'-amino oligonucleotides wherein the cleavage of the oligonucleotides from the support and the removal of their base protective groups can be conducted under mild alkaline conditions and wherein the 3'-amino oligonucleotides are obtained as single diastereoisomers free from side products. The solid supports described herein contain an ortho-hydroxymethyl benzoyl protective group (HMB-group) for the amino function wherein the hydroxymethyl group is employed for the attachment of the protective group to the solid phase of the support and the carbonyl group of the benzoyl moiety serves as the conjugation point for the amino-oligonucleotide. The HMB-group may optionally contain additional substituents in the aromatic ring.

The solid supports of the invention include, but are not limited to, compounds having the structure illustrated by formula (2)

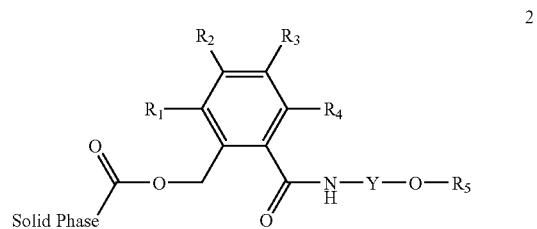

wherein
$R_1$, $R_2$, $R_3$ and $R_4$ are independently selected from the group consisting of H, alkyl with up to 4 carbon atoms, heteroalkyl with up to 4 carbon atoms, phenyl, alkoxy with up to 4 carbon atoms, heteroalkoxy with up to 4 carbon atoms, carboxy, alkyloxycarbonyl with up to 4 carbon atoms in the alkyl chain, alkylcarbamoyl with up to 4 carbon atoms in the alkyl chain, halo, cyano, nitro, sulfo and alkylsulfonyl with up to 4 carbon atoms in the alkyl chain;

$R_5$ is H or a protective group that is removed in the first deblocking step of a solid phase oligonucleotide synthesis; and Y is an organic spacer group comprising a straight or branched chain of one or more methylene groups, wherein the chain is optionally interrupted by one or more moieties independently selected from the group consisting of oxygen atoms, carbonyl groups, amide groups, ureido groups, urethane groups and aryl groups.

The novel solid supports described herein can be employed to synthesize 3'-amino oligonucleotides by conducting an oligonucleotide synthesis on the support and cleaving the oligonucleotide from the support under conditions suitable for the removal of the base protective groups. The HMB group is attached to the solid phase of the support through an ester function, which is labile under alkaline conditions and which is cleaved under the conditions employed to remove the base protective groups of the oligonucleotide. The cleavage of the ester function provides a hydroxymethyl group in the ortho-position relative to the carbonyl group of the benzoyl moiety. While not limited by theory, it is assumed that the hydroxymethyl group then participates in the release of the amino function from the benzoyl moiety via neighbor group assistance, thus facilitating the cleavage. A proposed mechanism for the release of 3'-amino oligonucleotides is depicted in Scheme 1. With reference to Scheme 1, upon treatment with base the support bound oligonucleotide (3) is released from the solid phase together with the HMB-group resulting in the production of intermediate (4). Intermediate (4) is then cleaved via neighbor group participation of the hydroxymethyl group to release the desired 3'-amino oligonucleotide. Phthalide (5) is formed as a byproduct of the reaction that may or may not be further cleaved in the alkaline reaction medium.

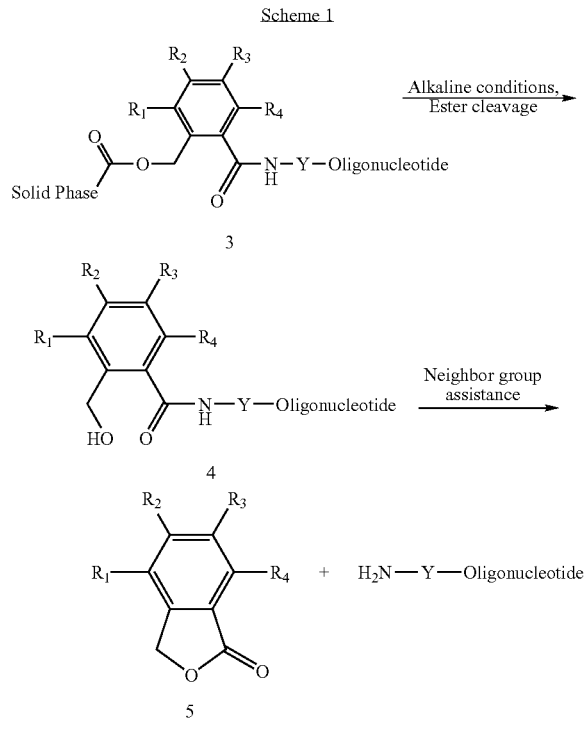

The following aspects of the solid supports disclosed herein are noteworthy:

A) The HMB-group constitutes the linker that connects the solid phase of the support with the oligonucleotide. It simultaneously serves as a protective group for the amino function that is introduced to the oligonucleotide. Thus, there is no separate protective group for the amino function that might be prone to side reactions, such as a premature deprotection. Once the amino protective group is cleaved, the 3'-amino oligonucleotide is released which eliminates the possibility of obtaining amino-acetylated side products during the capping steps of the oligonucleotide synthesis.

B) The spacer Y does not contain a chiral center, and therefore the resulting 3'-amino oligonucleotide products are not mixtures of diastereoisomers. Thus, they are detected as single peaks in chromatograms and their applications are not complicated by the presence of isomeric products.

C) The neighbor group participation of the hydroxymethyl group facilitates the cleavage of the benzoyl moiety from the amino function. The conditions necessary to completely cleave the HMB-group from 3'amino oligonucleotides are therefore mild and compatible with standard deprotection conditions for oligonucleotides.

D) The choice of the substituents $R_1$, $R_2$, $R_3$ and $R_4$ influences the stability of the HMB group and the conditions necessary for its complete removal from 3'-amino oligonucleotides. An electronegative substituent will increase the lability of the HMB-group and will therefore lead to milder cleavage conditions. The supports (2) can therefore be adapted to the nature of the synthesized oligonucleotide in order to match the conditions of its base deprotection.

Acylated HMB groups have been employed to protect amino functions as described by Cain (1976) J. Org. Chem. 41:2029-2031, and to protect the exocyclic amino groups of nucleobases as described by Kuijpers et al. (1990) Tetrahedron Letters 31:6729-6732 and (1993) Nucleic Acids Res. 21:3493-3500, each of which is incorporated herein by reference in its entirety. It is not believed, however, that they have ever been applied as linkers on solid phases to provide solid supports for the synthesis of amino-oligonucleotides.

The carboxylic ester function of the solid supports (2) described herein is characterized in that the carbonyl group of the ester function is linked to the solid phase as an aliphatic ester function or an aromatic ester function or as a carbonate, as displayed in the structures (6), (7) and (8), respectively. All of these groups are cleavable under standard deprotection conditions and result in the formation of hydroxymethyl groups that can assist in the further cleavage of the HMB group via neighbor group participation.

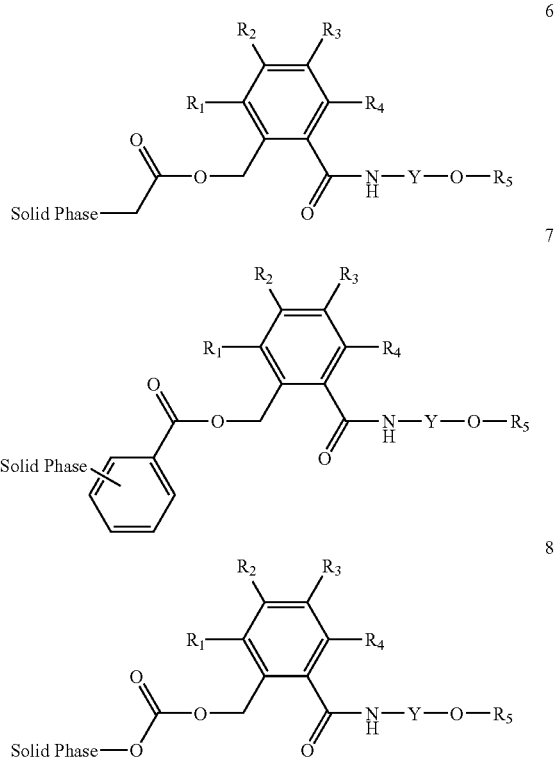

In preferred embodiments of the present invention, the principle of the HMB linker element of the solid supports (2) is applied to methods for the attachment of a nucleoside to a solid phase. The HMB linker element can substitute for a nucleoside in all variations of such methods. In the related supports for the synthesis of 3'-amino oligonucleotides the nucleoside is replaced by the HMB linker element. Examples of such variations include, but are not limited to a succinate linkage as displayed in structure (9), an oxalyl linkage as displayed in structure (10), a diglycolate linkage as displayed in structure (11) and a Q-linker variation (hydroquinone-O,O'-diacetic acid linker) as displayed in structure (12). Each of these variations is characterized in that the solid phase is conjugated to a carboxylic acid which is esterified to the HMB linker element at its hydroxymethyl group.

method is to prepare an ester of the HMB linker structure (13) with a dicarboxylic acid, such as succinic acid, diglycolic acid, or hydroquinone-O,O'-diacetic acid, which in turn is conjugated to an amino- or hydroxyl-derivatized solid phase. The conjugation could be effected through a condensing agent or, if the dicarboxylic acid derivative is conjugated to an amino derivatized support, through an active ester of the dicarboxylic acid derivative, such as a pentafluorophenyl ester, a trichlorophenyl ester or a p-nitrophenyl ester.

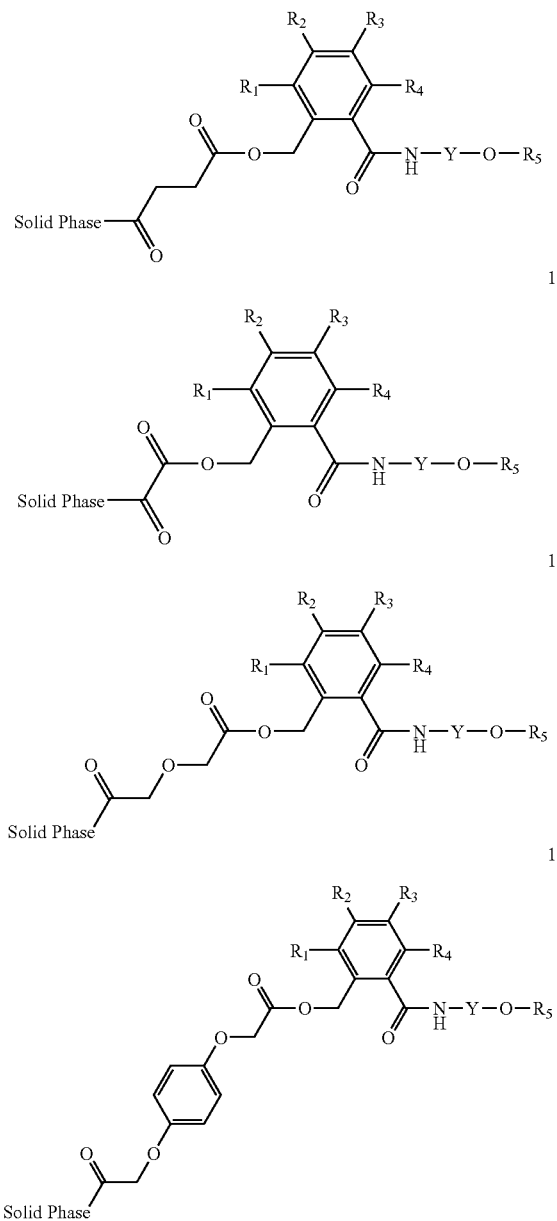

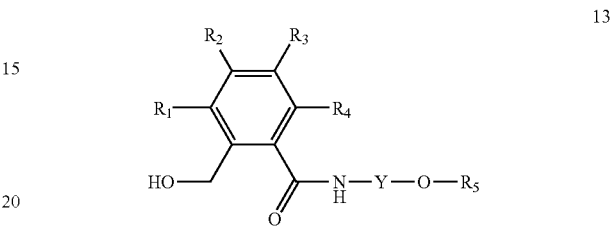

The identity of the solid phase of support (2) carrying the HMB group is not critical to the present invention. The solid phase can be any solid phase that is applicable in oligonucleotide synthesis. Examples of such solid phases include, but are not limited to CPG (controlled pore glass), silica, cellulose, polystyrene, composite materials of polystyrene and polyethylene glycols (PEG-PS or Tentagel-materials), methacrylate and methacrylate copolymers such as FRACTOGEL®, or any other solid phase that is suitable in a solid phase oligonucleotide synthesis.

In a preferred embodiment of the present invention the solid phase is CPG (controlled pore glass). Examples of CPG supports that are useful for the synthesis of 3'-amino oligonucleotides are illustrated by structures (14) and (15).

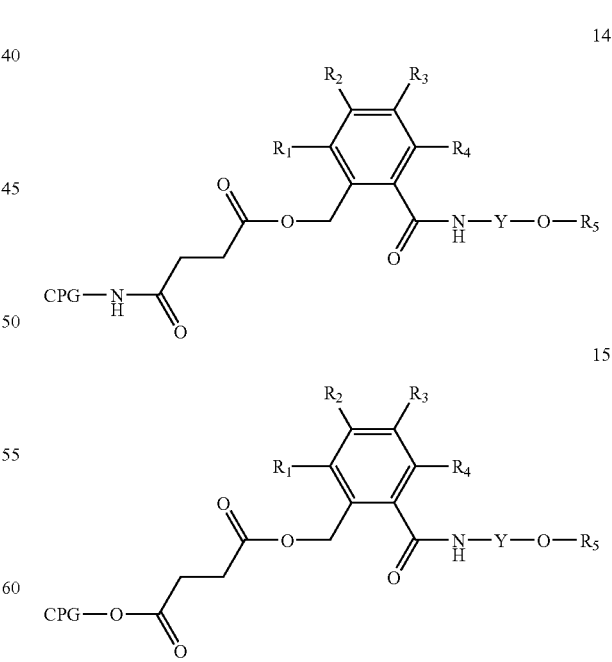

Solid supports (9), (10), (11) and (12) can be prepared by a variety of methods that mimic the loading of nucleosides to solid phases and that are known to those skilled in the art. One method involves the condensation of the hydroxyl group of the HMB structure (13) with a carboxylic acid on the solid phase in the presence of a condensing agent, such as DCC (dicyclohexylcarbodiimide), EDC (N,N-dimethylaminoethylpropylcarbodiimide), HBTU (O-benzotriazolyl-1-yl-N,N,N',N'-tetramethyluronium hexafluorophosphate), HATU (O-(7-azabenzotriazol-1-yl)-N,N,N',N'-tetramethyluronium hexafluorophosphate) or other condensing agents for the formation of esters from carboxylic acids and alcohols. Similar condensation reactions are well known in the art with a great variety of condensing agents. Another The spacer group Y may contain any number of atoms, including but not limited to 100 or more atoms. In a preferred embodiment of the present invention, the spacer group Y contains 3 to 10 atoms and in a particularly preferred embodiment the spacer contains 5 or 6 atoms. Spacer group Y is comprised of methylene units and optional oxygen atoms and/or various functional groups, such as carbonyl, amide, ureido, urethane or aromatic groups. In a preferred embodiment, Y is —(CH$_2$)$_n$— with n ranging from 3 to 11, or —CH$_2$—CH$_2$—(O—CH$_2$—CH$_2$)$_n$— with n ranging from 1 to 3. In a particularly preferred embodiment, Y is —(CH$_2$)$_6$— or —CH$_2$—CH$_2$—O—CH$_2$—CH$_2$—.

In a preferred embodiment of the invention R$_5$ is an acid labile protective group. Suitable acid labile protective groups will be apparent to those skilled in the art and include, but are not limited to those acid labile protective groups discussed for protecting hydroxyl groups by Wuts and Greene in *Protective Groups in Organic Synthesis*, Wiley Interscience, ISBN 0471160199. Acid labile protective groups that are suitable in the context of the present invention are sufficiently labile such that they may be removed under conditions which do not degrade nucleic acids. Examples of preferred acid labile protective groups include, but are not limited to substituted trityl groups, e.g. pixyl-, monomethoxytrityl- or dimethoxytrityl groups, or tetrahydropyrayl groups, e.g. tetrahydrpyran-2-yl and 4-methoxytetrahydropyran-2-yl. A particularly preferred acid labile protective group is a dimethoxytrityl group, especially the 4,4'-dimethoxytrityl group.

The preparation of two illustrative solid supports for the synthesis of 3'-amino oligonucleotides according to the method of this invention is set forth in Scheme 2 and described in Examples 1 and 2. With reference to Scheme 2, 1-dimethoxytrityl-6-amino-hexan-1-ol (16) is reacted with either phthalide (17) or 6-nitrophthalide (18) under Lewis-acid catalysis to give the substituted ortho-hydroxymethyl benzamides (19) and (20), respectively. Compounds (19) and (20) are then reacted with succinic anhydride and triethylamine in ethyl acetate under catalysis by dimethylaminopyridine (DMAP) to provide the carboxylic acids (21) and (22), respectively. Compounds (21) and (22) are then esterified with 4-nitrophenol in the presence of DCC to provide the active esters (23) and (24). The active esters (23) and (24) are employed in loading amino CPG with a C6-spacer to produce solid supports (25) and (26).

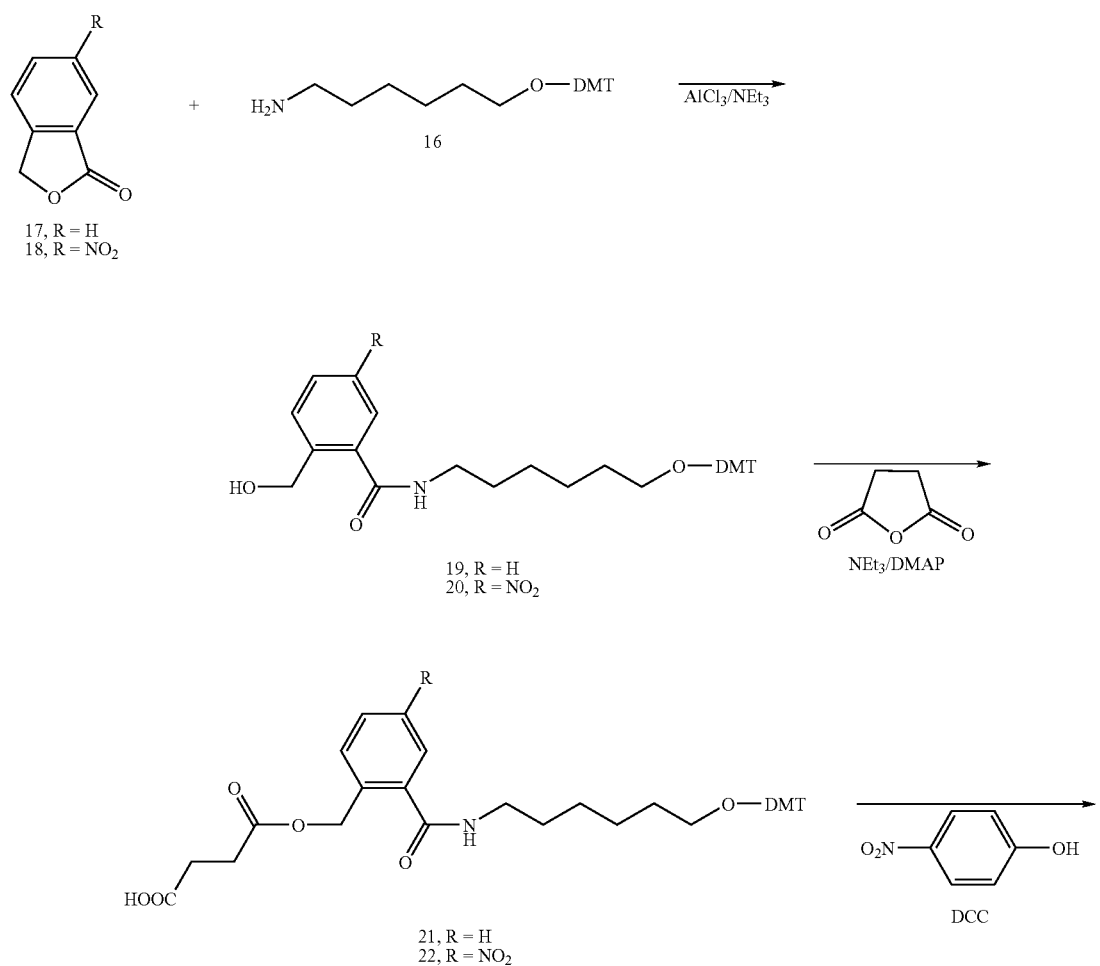

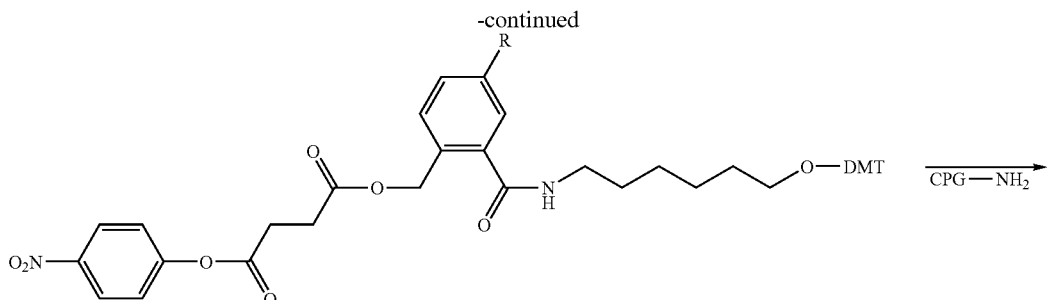

23, R = H
24, R = NO₂

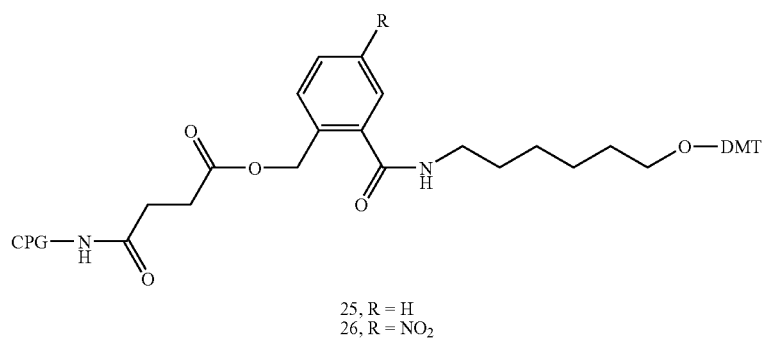

25, R = H
26, R = NO₂

The novel method of the invention for the synthesis of 3'-amino oligonucleotides is illustrated in Scheme 3 and Example 3. The model oligonucleotide 3'-amino d(T$_{10}$) (27) was prepared with commercial synthesis reagents using protocols supplied by the manufacturer of the synthesizer on both supports. The oligonucleotide products were cleaved from the support with concentrated ammonia for 45 minutes at room temperature and further incubated in concentrated ammonia at 55° C. overnight. The analysis of the crude products by MALDI-TOF mass spectroscopy and anion exchange HPLC confirmed the identity of the expected 3'-amino oligonucleotide (27) and demonstrated the effectiveness of the method. The purity of the 3'-amino oligonucleotide was 93% for the product prepared on solid support (25) and 91% for the product prepared on support (26). The anion exchange chromatogram of the oligonucleotide prepared on support (25) is depicted in FIG. 1 for illustrative purposes.

Scheme 3

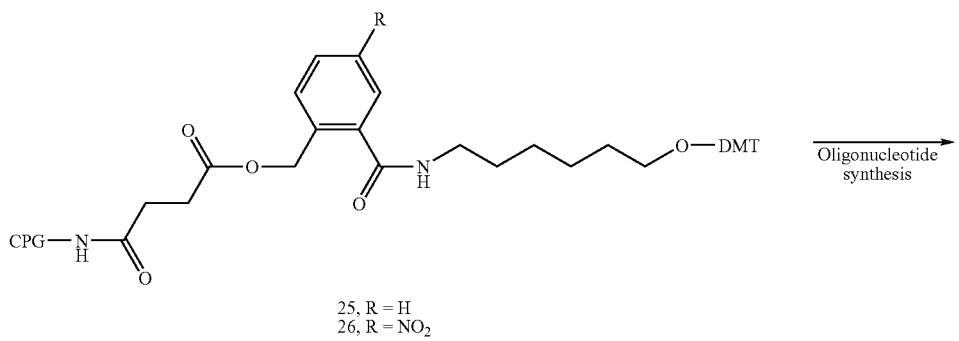

25, R = H
26, R = NO₂

-continued

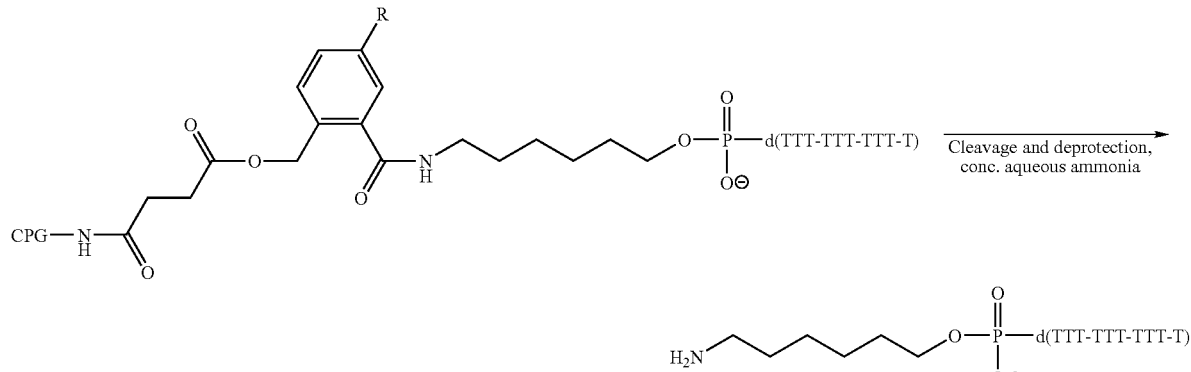

3'-Amino oligonucleotides prepared on supports (25) and (26) can be completely released from the support and from the HMB linker element under mild conditions as illustrated in Examples 4 to 6. 60 Minutes of incubation in concentrated aqueous ammonia at room temperature was determined to be fully sufficient to release an oligonucleotide product from support (26) as described in Example 4. The time for the complete cleavage of the HMB linker element from oligonucleotides in concentrated aqueous ammonia at 55° C. was determined to be 6 hours for oligonucleotides prepared on support (25) and 2 hours for oligonucleotides prepared on support (26). Anion exchange chromatograms of the model oligonucleotide sequence 3'-amino d($T_{10}$) (27) (SEQ ID NO:1) obtained after incubation of the support bound oligonucleotide in concentrated aqueous ammonia at 55° C. for various times are depicted in FIG. 2 for illustrative purposes. FIG. 2 shows that the HMB element is already cleaved from the 3'-amino oligonucleotide to a great extent (>90%) after incubation for 1 hour. The expected product with the free amino group is already the main peak in the chromatogram at a retention time of approximately 16 minutes with greater than 80% peak area. There is, however, a small amount of HMB-oligonucleotide conjugate at approximately 19 minutes retention time, which is no longer observable after incubation for 2 hours. The chromatogram from the incubation for 4 hours is unchanged compared to the chromatogram obtained from the incubation for 2 hours. FIG. 3 shows that there is a plateau reached for the cleavage reaction after approximately 90 minutes incubation time in concentrated ammonia at 55° C.

The difference in the time for a complete cleavage of the HMB elements from the oligonucleotides prepared on supports (25) and (26) can be explained through the nature of the substituents on the aromatic ring of the HMB group. Support (25) carries four hydrogen substituents, whereas support (26) carries three hydrogen substituents and one nitro substituent. The nitro group is an electron withdrawing substituent that is expected to lower the electron density in the aromatic ring and also to lower the electron density of the carbonyl carbon of the HMB element through an inductive and/or mesomeric effect. The lower electron density at the carbonyl carbon of support (26) compared to the carbonyl carbon of support (25) facilitates the neighbor group assisted cleavage of the HMB element from the amino function and therefore results in shorter cleavage times under otherwise identical conditions. Electron withdrawing substituents generally reduce the electron density at the carbonyl carbon and lead to shorter cleavage times and therefore milder deprotection conditions.

Example 5 demonstrates that support (25) is fully compatible with standard deprotection conditions. Oligonucleotides in which the nucleobases are protected with benzoyl groups for adenine and cytidine bases and with isobutyryl groups for guanine bases are conveniently deprotected in concentrated aqueous ammonia at 55° C. for 8 hours. The HMB linker element is completely removed from oligonucleotides prepared on support (25) under such conditions and longer deprotection times as required with many of the supports for the synthesis of 3'-amino oligonucleotides that are described in the prior art are not necessary. Example 6 demonstrates that support (26) is fully compatible with synthesis schemes for oligonucleotides wherein the nucleobases carry protective groups that allow the complete deprotection of the synthesized oligonucleotides within 2 hours at 55° C. in concentrated ammonia. Such synthetic schemes are very useful to reduce the total synthesis time for oligonucleotides and to increase the throughput in oligonucleotide synthesis facilities. Examples of synthesis schemes that allow the complete deprotection of oligonucleotides within 2 hours in concentrated aqueous ammonia at 55° C. include, but are not limited to the following combinations of base protective group combinations:

A) benzoyl (bz) for A and C, N,N-dimethylformamidine (dmf) for G;
B) phenoxyacetyl (PAC) for A and G, isobutyryl (ib) for C; and
C) 4-(tert-butylphenoxy)acetyl (TAC) for A, C and G.

All of the above combinations of base protective groups and also all combinations of base protective groups that include benzoyl, phenoxyacetyl or 4-(tert-butylphenoxy)acetyl protection for A; benzoyl, isobutyryl, acetyl, 4-(tert-butylphenoxy)acetyl protection for C; and phenoxyacetyl or 4-(tert-butylphenoxy)acetyl or N,N-dimethylformamidine for G are compatible with the application of support (26).

The compatibility of support (26) with an oligonucleotide synthesis scheme wherein benzoyl is applied as protective group for adenine and cytidine bases and N,N-dimethylformamidine is applied as protective group for guanine bases is described for purposes of illustration in Example 7. Briefly, the 17-mer heterosequence 5'-d(CTC-TCA-GCG-AGC-CTC-AA)-3' was synthesized on support (26) and the resulting 3'-amino oligonucleotide product (28) (SEQ ID NO:2)

was deprotected by incubation in concentrated aqueous ammonia at 55° C. for 2 hours. The 3'-amino oligonucleotide was obtained in 80% purity as determined by anion exchange chromatography. The identity of the product was confirmed by MALDI-TOF mass spectroscopy. The anion exchange chromatogram of the crude 3'-amino oligonucleotide (28) obtained in Example 7 is depicted in FIG. 4.

28

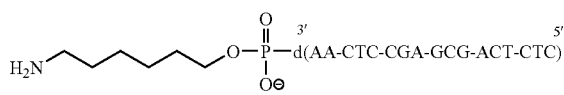

The supports of the present invention are fully compatible with the standard phosphoramidite synthetic method for the preparation of oligonucleotides. In particular, there is no premature cleavage of the HMB linker element during any of the chemical steps and reaction conditions that are employed in a synthesis cycle to attach a new monomer to the support. Premature cleavage would result in the concomitant release of partly synthesized oligonucleotides which would reduce the yield of the 3'-amino oligonucleotide products. The compatibility with the chemical steps and reaction conditions of the phosphoramidite method is demonstrated in Example 8. In this example, a commercial thymidine loaded support and support (26) were mixed together in a 1:1 ratio with respect to their loading and the resulting mixture of supports was used together in one synthesis column to prepare a mixture of oligonucleotides with a commercial DNA/RNA synthesizer. Both supports were coupled with the same monomer phosphoramidite and subjected to the same reagents in this experiment since they were applied together in the same column. The resulting oligomeric products were obtained by programming a d($T_{15}$) sequence into the instrument and running the corresponding synthesis under conditions as recommended by the manufacturer of the instrument. The expected products are a 3'-amino-d($T_{14}$) (SEQ ID NO:3) sequence that is assembled on support (26) and a d($T_{15}$) (SEQ ID NO:4) sequence that is assembled on the commercial dT-support in a 1:1 ratio. The mixture of crude oligonucleotide products was analyzed by anion-exchange HPLC and the ratio of the two products was examined taking into account that the d($T_{15}$)-product from the thymidine loaded support was a slightly stronger absorbant due to the presence of one additional nucleotide in the product compared to the 3'-amino-d($T_{14}$)-product from support (26). A ratio of 0.96:1.00 was obtained for the products 3'-amino-d($T_{14}$) and d($T_{15}$), the corresponding anion exchange HPLC chromatogram is depicted in FIG. 5. The d($T_{15}$)-oligonucleotide is observed at approximately 17.5 minutes retention time in the chromatogram, whereas the 3'-amino-d($T_{14}$)-product is observed at a retention time of approximately 15 minutes, which can be explained by the lower charge of the 3'-amino oligonucleotide due to the presence of the free amino group that is protonated under the conditions of the analysis and compensates one of the negative charges from the phosphate backbone of the oligonucleotide. A similar experiment was conducted with a d($T_{30}$)-sequence programmed in the synthesizer and a ratio of 0.95:1.00 was observed for the expected oligonucleotide products 3'-amino-d($T_{29}$) and d($T_{30}$). Both experiments clearly demonstrate that 3'-amino oligonucleotide products from support (26) are, within the limits of error, obtained in the same yield as oligonucleotides from commercial nucleoside loaded supports and that there is no premature cleavage of the HMB linker element with a concomitant loss of oligonucleotide products in the case of support (26). The support (26) is therefore fully compatible with the standard phosphoramidite synthesis of oligonucleotides.

The usefulness of the methods and supports that are disclosed in this invention is further illustrated through the application of 3'-amino oligonucleotides in post-synthetic labeling reactions. The oligonucleotide 3'-amino-d($T_{10}$) (27) is derivatized with the reporter dye tetramethylrhodamine (TAMRA) in the Examples 9 and 10. The 3'-amino oligonucleotide (27) was prepared on support (25) in Example 9. The oligonucleotide was incubated in aqueous conc. ammonia for 6 hours at 55° C. to afford the complete cleavage of the HMB linker element in this example. The crude product was used as such for the labeling reaction and the reaction products were analyzed by anion exchange chromatography. The labeled oligonucleotide was obtained in high purity (69%) and its identity was confirmed by MALDI-TOF mass spectroscopy. In Example 10, the 3'-amino oligonucleotide (27) was prepared on support (26) and the oligonucleotide was incubated in aqueous concentrated ammonia for 2 hours at 55° C. to afford the complete cleavage of the HMB linker element in this example. The crude product was used as such for the labeling reaction and the reaction products were analyzed by anion exchange chromatography. The labeled oligonucleotide was obtained in high purity (81%) and its identity was confirmed by MALDI-TOF mass spectroscopy. The results from the above labeling experiments demonstrate that 3'-amino oligonucleotides prepared on the supports of the present invention can be nearly completely conjugated to active esters in post synthetic labeling reactions.

In conclusion, the novel methods for the synthesis of 3'-amino oligonucleotides and the novel solid supports of the invention fulfill the complete set of desired criteria for such methods and supports in that:

A) they are compatible with and stable under the standard phosphoramidite synthetic method for oligonucleotides;

B) the supports comprise a linkage to the oligonucleotide that is cleaved during the deprotection of the nucleobases, wherein the cleavage does not require the introduction of reagents which are not commonly employed in the deprotection of oligonucleotides;

C) the supports are cleavable from the oligonucleotide in a reaction time that is comparable to the time employed in standard deprotection conditions for the removal of base protective groups, or which is even shorter and therefore allows the use of oligonucleotide synthesis schemes wherein the bases are protected by groups that can be removed in aqueous conc. ammonia at 55° C. in 2 hours;

D) they provide the 3'-amino oligonucleotide without side products derived from modifications of the amino group, e.g. acylations of the amine;

E) they do not generate diasteromeric mixtures of oligonucleotides, because the corresponding supports do not introduce chiral centers to the oligonucleotides; and F) the supports are preparable in a simple and efficient manner.

The novel methods and solid supports of the invention are therefore superior to the methods and supports of the prior art, because they combine all the listed desired features, a need that to date is unmet by the commercially available reagents and the reagents described in the scientific literature.

EXAMPLES

Example 1

Synthesis of Solid Support (25) (Scheme 2)

ortho-Hydroxymethyl benzamide (19). A solution of triethylamine (TEA, 0.824 g, 1.13 ml, 8.14 mmol, 1.5 equiv.) in 1,2-dichloroethane (3 ml) was added dropwise under stirring and cooling with ice to a suspension of $AlCl_3$ (0.796 g, 5.97 mmol, 1.1 equiv.) in 1,2-dichloroethane (7 ml). The temperature was maintained at 15-20° C. during the addition and the mixture was then allowed to warm up at room temperature. A solution of 1-dimethoxytrityl-6-aminohexan-1-ol (16) (2.505 g, 5.97 mmol, 1.1 equiv., prepared as described by Woo and Fung (1996), International Pat. App. Pub. No. WO 96/05215, which is incorporated herein by reference in its entirety) and phthalide (17) (0.728 g, 5.43 mmol, 1.0 equiv.) in 1,2-dichloroethane (3 ml) was added over a period of 20 min and the mixture was stirred at room temperature overnight. The completion of the reaction was confirmed by TLC analysis (EtOAc containing 1% TEA). The reaction mixture was then quenched with an ice-water mixture (30 ml) and stirred for further 30 min. The resulting suspension was filtered through a bed of Celite® and the filter cake was washed with 1,2-dichloroethane (10 ml). The organic phase of the combined filtrates was separated, washed with water (30 ml) and brine (20 ml), dried over $MgSO_4$ and concentrated. The crude product was purified by flash chromatography (15-70% EtOAc in hexanes containing 1% of TEA, gradient elution) yielding 0.80 g (27%) of compound (19) as a pale yellow oil. $R_f=0.68$ (EtOAc containing 1% TEA). $^1$H NMR (400 MHz, $CD_3CN$) δ 7.61-7.19 (m, 14H), 6.85 (d, J=8.9 Hz, 4H), 5.33 (s, 1H), 4.50 (s, 2H), 3.75 (s, 6H), 3.32 (q, J=6.6 Hz, 2H), 3.01 (t, J=6.6 Hz, 2H), 1.63-1.53 (m, 4H), 1.44-1.28 (m, 4H).

Carboxylic acid (21). The ortho-hydroxymethyl benzamide (19) (800 mg, 1.445 mmol, 1.0 equiv.) was dried by coevaporation with THF and dissolved in 3 ml ethyl acetate. Triethylamine (TEA, 143 mg, 0.20 ml, 1.416 mmol, 0.98 equiv.), succinic anhydride (174 mg, 1.734 mmol, 1.2 equiv.) and 4-dimethylaminopyridine (44 mg, 0.361 mmol, 0.25 equiv.) were added. The mixture was kept at 50° C. until TLC analysis (EtOAc containing 1% TEA) indicated the completeness of the reaction. The mixture was evaporated to dryness under vacuum, dissolved in 10 ml dichloromethane and extracted with 10 ml 10% citric acid in water and with 10 ml water. The organic phase was dried over sodium sulfate, filtered and evaporated to yield 700 mg (74%) of the carboxylic acid (21) as a light yellow foam. $R_f=0.05$ (EtOAc containing 1% TEA). $^1$H NMR (300 MHz, $CD_3CN$) δ 7.47-7.20 (m, 13H), 6.90-6.86 (m, 4H), 5.26 (s, 2H), 3.78 (s, 6H), 3.31 (q, J=6.6 Hz, 2H), 3.03 (t, J=6.4 Hz, 2H), 2.61-2.53 (m, 4H), 1.66-1.52 (m, 4H), 1.48-1.25 (m, 4H). $^{13}$C NMR (75 MHz, $CD_3CN$) δ 173.2, 172.3, 168.8, 158.8, 145.9, 136.9, 136.6, 134.6, 130.1, 129.0, 128.3, 128.0, 127.5, 126.9, 113.2, 85.8, 64.1, 63.3, 55.1, 39.5, 29.9, 29.4, 29.0, 28.5, 26.7, 26.0.

Active ester (23). The carboxylic acid (21) (700 mg, 1.071 mmol, 1.0 equiv.) was dissolved in 10 ml dry 1,4-dioxane and 0.21 ml dry pyridine. 4-Nitrophenol (152 mg, 1.092 mmol, 1.02 equiv.) and 1,3-dicyclohexylcarbodiimide (287 mg, 1.392 mmol, 1.3 equiv.) were added and the reaction mixture was stirred at room temperature until TLC analysis (EtOAc containing 1% TEA) confirmed the completion of the reaction. A white precipitate formed during the reaction. The precipitate was filtered off and the filtrate was evaporated to dryness. The active ester (23) was obtained as a pale yellow foam, which was not purified and used as such in the next step for the loading of CPG, yield 800 mg (96%). $R_f=0.78$ (EtOAc containing 1% TEA). $^1$H NMR (300 MHz, $CD_3CN$) δ 8.25-8.22 (m, 2H), 7.47-7.22 (m, 14H), 6.91-6.83 (m, 6H), 5.31 (s, 2H), 3.77 (s, 6H), 3.31 (q, J=6.5 Hz, 2H), 3.01 (t, J=6.4 Hz, 2H), 2.89 (t, J=6.7 Hz, 2H), 2.75 (t, J=6.7 Hz, 2H), 1.65-1.50 (m, 4H), 1.48-1.21 (m, 4H). $^{13}$C NMR (75 MHz, $CD_3CN$) δ 172.2, 171.0, 169.1, 159.0, 156.0, 146.1, 145.9, 137.1, 136.8, 134.7, 130.4, 129.4, 128.6, 128.5, 128.2, 127.8, 127.1, 126.5, 125.6, 123.2, 113.4, 86.0, 64.6, 63.5, 55.3, 39.8, 30.1, 29.6, 29.5, 29.2, 27.0, 26.3.

Solid support (25). Amino-CPG 500 Å with a $C_6$-spacer (4.0 g) was washed with dry acetonitrile and dried under high vacuum overnight. The CPG was then transferred into a 25 ml solid phase synthesis reactor that was sealed with a septum, flushed with argon and charged with DMF (12.6 ml) and triethylamine (TEA, 0.4 ml). The active ester (23) (186 mg, 240 µmol) was weighed into a 4 ml screw cap vial, dissolved in DMF (1.0 ml) and added to the suspension, which was then shaken overnight at room temperature. The CPG was washed with DMF/TEA (9:1, v/v, 4×40 ml), DMF (4×40 ml), ethanol (3×40 ml), acetonitrile (2×40 ml) and ethyl acetate (3×40 ml). The CPG was dried overnight under high vacuum. The loading was determined to be 58.3 µmol/g by a photometric (497 nm) DMT loading assay with 3% TCA in dichloromethane.

Example 2

Synthesis of Solid Support (26)

ortho-Hydroxymethyl benzamide (20). A solution of triethylamine (TEA, 0.658 g, 0.91 ml, 6.50 mmol, 1.5 equiv.) in 1,2-dichloroethane (3 ml) was added dropwise under stirring and cooling with ice to a suspension of $AlCl_3$ (0.635 g, 4.76 mmol, 1.1 equiv.) in 1,2-dichloroethane (7 ml). The temperature was maintained at 15-20° C. during the addition and the mixture was then allowed to warm up at room temperature. A solution of 1-dimethoxytrityl-6-aminohexan-1-ol (16) (2.00 g, 4.76 mmol, 1.1 equiv., prepared as described by Woo and Fung (1996), International Pat. App. Pub. No. WO 96/05215) and 6-nitrophthalide (18) (0.766 g, 4.33 mmol, 1.0 equiv.) in 1,2-dichloroethane (3 ml) was added over a period of 20 min and the mixture was stirred at room temperature overnight. The completion of the reaction was confirmed by TLC analysis (EtOAc containing 1% TEA). The reaction mixture was then quenched with an ice-water mixture (30 ml) and stirred for an additional 30 min. The resulting suspension was filtered through a bed of Celite® and the filter cake was washed with 1,2-dichloroethane (10 ml). The organic phase of the combined filtrates was separated, washed with water (30 ml) and brine (20 ml), dried over $MgSO_4$ and concentrated. The crude product was purified by flash chromatography (35-75% EtOAc in hexanes, gradient elution) yielding 0.20 g (8%) of compound (20) as a pale yellow oil. $R_f=0.2$ (hexanes/EtOAc 1:1, v/v, containing 1% TEA). $^1$H NMR (300 MHz, $CD_3CN$) δ 8.32-8.27 (m, 2H), 7.76-7.73 (m, 1H), 7.47-7.44 (m, 2H), 7.33-7.20 (m, 8H), 6.87 (d, J=9.1 Hz, 4H), 4.69 (d, J=5.9 Hz, 2H), 4.14 (t, J=5.9 Hz, 1H), 3.77 (s, 6H), 3.35 (q, J=6.5 Hz, 2H), 3.03 (t, J=6.4 Hz, 2H), 1.64-1.55 (m, 4H), 1.43-1.28 (m, 4H). $^{13}$C NMR (75 MHz, $CD_3CN$) δ 167.4, 158.8, 147.7, 145.9, 136.9, 130.1, 128.2, 128.0, 126.9, 125.1, 122.9, 113.2, 85.8, 63.3, 62.3, 55.1, 39.8, 29.8, 29.1, 26.7, 26.0.

Carboxylic acid (22). The ortho-hydroxymethyl benzamide (20) (200 mg, 0.334 mmol, 1.0 equiv.) was dried by coevaporation with THF and dissolved in 1.5 ml ethyl acetate. Triethylamine (TEA, 46 µl, 0.327 mmol, 0.98 equiv.), succinic anhydride (40 mg, 0.401 mmol, 1.2 equiv.) and 4-dimethylaminopyridine (10 mg, 0.084 mmol, 0.25 equiv.) were added. The mixture was kept at 50° C. until TLC analysis (EtOAc containing 1% TEA) indicated the completion of the reaction. The mixture was evaporated to dryness under vacuum, dissolved in 10 ml dichloromethane and extracted with 10 ml 10% citric acid in water and with 10 ml water. The organic phase was dried over sodium sulfate, filtered and evaporated to yield 245 mg (95%) of the carboxylic acid (22) as a pale yellow foam. $R_f$=0.05 (EtOAc containing 1% TEA). $^1$H NMR (300 MHz, $CD_3CN$) δ 8.29-8.26 (m, 2H), 7.73-7.70 (m, 1H), 7.47-7.43 (m, 2H), 7.35-7.22 (m, 7H), 7.13 (t, J=6.7 Hz, 1H), 6.89-6.84 (m, 4H), 5.36 (s, 2H), 3.77 (s, 6H), 3.34 (q, J=6.6 Hz, 2H), 3.03 (t, J=6.4 Hz, 2H), 2.68-2.56 (m, 4H), 1.66-1.52 (m, 4H), 1.47-1.32 (m, 4H). $^{13}$C NMR (75 MHz, $CD_3CN$) δ 173.4, 172.5, 166.9, 159.0, 147.6, 146.2, 142.6, 137.1, 130.4, 129.7, 129.5, 128.5, 128.2, 128.1, 127.1, 125.0, 122.8, 113.4, 86.0, 63.6, 63.5, 55.4, 40.0, 30.1, 29.4, 29.2, 28.6, 27.0, 26.2.

Active ester (24). The carboxylic acid (22) (245 mg, 0.351 mmol, 1.0 equiv.) was dissolved in 3 ml dry 1,4-dioxane and 70 µl dry pyridine. 4-Nitrophenol (50 mg, 0.358 mmol, 1.02 equiv.) and 1,3-dicyclohexylcarbodiimide (94 mg, 0.456 mmol, 1.3 equiv.) were added and the reaction mixture was stirred at room temperature until TLC analysis (EtOAc containing 1% TEA) confirmed the completion of the reaction. A white precipitate formed during the reaction. The precipitate was filtered off and washed with 1,4-dioxane. The combined filtrates were evaporated to dryness. The active ester (24) was obtained as a light yellow foam, which was not purified and used as such in the next step for the loading of CPG, yield 250 mg (87%). $R_f$=0.73 (EtOAc containing 1% TEA). $^1$H NMR (300 MHz, $CD_3CN$) δ 8.28-8.21 (m, 3H), 7.72-7.70 (m, 1H), 7.46-7.42 (m, 2H), 7.35-7.13 (m, 10H), 6.88-6.84 (m, 4H), 5.40 (s, 2H), 3.76 (s, 6H), 3.33 (q, J=6.6 Hz, 2H), 3.02 (t, J=6.4 Hz, 2H), 2.94-2.90 (m, 2H), 2.83-2.79 (m, 2H), 1.66-1.52 (m, 4H), 1.48-1.32 (m, 4H). $^{13}$C NMR (75 MHz, $CD_3CN$) δ 172.8, 172.2, 166.8, 159.0, 156.0, 147.6, 146.1, 146.0, 142.4, 137.1, 130.9, 129.9, 128.5, 128.2, 127.1, 125.7, 125.0, 123.2, 122.8, 113.4, 86.0, 63.9, 63.5, 55.3, 40.0, 30.1, 29.5, 29.4, 29.1, 27.0, 26.2. MS (FAB) m/z 819 $[M+H]^+$.

Solid support (26). Amino-CPG 500 Å with a $C_6$-spacer (5.0 g) was washed with dry acetonitrile and dried under high vacuum overnight. The CPG was then transferred into a 25 ml solid phase synthesis reactor that was sealed with a septum, flushed with argon and charged with DMF (13 ml) and triethylamine (TEA, 0.5 ml). The active ester (24) (250 mg, 305 µmol) was weighed into a 10 ml screw cap vial, dissolved in DMF (4.0 ml) and added to the suspension, which was then shaken overnight at room temperature. The CPG was washed with DMF/TEA (9:1, v/v, 3×20 ml), DMF (4×20 ml), ethanol (3×20 ml), acetonitrile (2×20 ml) and ethyl acetate (3×20 ml). The CPG was dried overnight under high vacuum. The CPG was incubated with 8.75 ml each of a commercial Cap A-(acetic anhydride in THF) and Cap B-(N-methylimidazole and pyridine in THF) DNA synthesis solution for 2 hours under shaking at room temperature. The CPG was washed with THF (20 ml), ethanol/pyridine (9/1, v/v, 3×20 ml), ethanol (3×20 ml), acetonitrile (2×20 ml) and ethyl acetate (3×20 ml). The CPG was dried overnight under high vacuum. The loading was determined to be 36.0 µmol/g by a photometric (497 nm) DMT loading assay with 3% TCA in dichloromethane.

Example 3

Synthesis of 3'-Amino Oligonucleotide d($T_{10}$) (27) on Solid Supports (25) and (26)

Solid supports (25) and (26), respectively, were packed in standard plastic synthesis columns suitable for ABI Expedite™ Model 8909 DNA/RNA synthesizer (support (25) 17.1 mg, loading 58.3 µmol/g, 1 µmol scale; support (26) 27.8 mg, loading 36.0 µmol/g, 1 µmol scale). The oligonucleotide 3'-amino-d($T_{10}$) (27) was synthesized on each support using an ABI Expedite™ Model 8909 DNA/RNA synthesizer with commercial dT-phosphoramidite and commercial synthesis solutions. Each synthesis was performed using protocols supplied by the manufacturer of the synthesizer in DMT-OFF mode. A dummy nucleotide was incorporated at the 3'-end of the sequence that was entered into the synthesizer. The oligonucleotide products were cleaved from the supports with conc. aqueous ammonia (32%) for 45 minutes at room temperature and further incubated in conc. ammonia at 55° C. over night. Both products were analyzed by anion-exchange HPLC on a Dionex DNAPac PA100 column (4×250 mm) eluting with a linear gradient from 10% to 46% B in 22.00 min at 85° C. with a flow rate of 1.5 ml/min, detection at λ=260 nm, buffer A=25 mM Trizma hydrochloride/1 mM EDTA/10% $CH_3CN$, pH 7.5, buffer B=25 mM Trizma hydrochloride/1 mM EDTA/10% $CH_3CN$/1 M NaCl, pH 7.5. The purity of the prepared oligonucleotide was 93% for the synthesis on support (25) and 91% for the synthesis on support (26). The chromatogram of the oligonucleotide product from the synthesis on support (25) is depicted in FIG. 1. The products were further characterized by MALDI-TOF mass spectrometry and their identity was confirmed by the observed mass (calcd 3159.1; found 3164.7 for the synthesis on support (25), found 3164.0 for the synthesis on support (26)). 65 $OD_{260}$ were obtained from the synthesis on support (25) and 86 $OD_{260}$ were obtained from the synthesis on support (26).

Example 4

Investigation of the Time Required to Completely Release the Oligonucleotide 3'-Amino-d($T_{10}$) (27) from Solid Support (26)

Solid support (26) was packed in a standard plastic synthesis column suitable for ABI Expedite™ Model 8909 DNA/RNA synthesizer (27.8 mg, loading 36.0 µmol/g, 1 µmol scale). The oligonucleotide 3'-amino-d($T_{10}$) (27) was synthesized using an ABI Expedite™ Model 8909 DNA/RNA synthesizer with commercial dT-phosphoramidite and commercial synthesis solutions. The synthesis was performed using protocols supplied by the manufacturer of the synthesizer in DMT-ON mode. A dummy nucleotide was incorporated at the 3'-end of the sequence that was entered into the synthesizer. An aliquot of the support bound oligonucleotide (0.8 mg CPG) was incubated in conc. aqueous ammonia at room temperature in a UV cuvette with a path length of 1 cm. Absorbance readings were taken at various times after gentle shaking. The absorbance readings increased over time and gradually approached a plateau after approximately 60 minutes with less than 10% further increase within the next 60 minutes. Other aliquots of the support bound oligonucleotide (approximately 5 mg each) were incubated with conc. aqueous ammonia at room temperature in separate vials for various times. The CPG from these experiments was collected by filtration, washed carefully with water and dried under vacuum. A photometric (497 nm) DMT loading assay with 3% TCA in dichloromethane was conducted with the dried supports. The observed loadings were 36.0 µmol/g without incubation in ammonia and 3.8 µmol/g, 3.4 µmol/g, 3.3 µmol/g and 3.4 µmol/g for incubation times in ammonia of 45 minutes, 60 minutes, 80 minutes and 120 minutes respectively.

Example 5

Investigation of the Time Required for the Complete Deprotection of the Oligonucleotide 3'-Amino-d($T_{10}$) (27) Prepared on Solid Support (25)

Solid support (25) was packed in a standard plastic synthesis columns suitable for ABI Expedite™ Model 8909 DNA/RNA synthesizer (17.1 mg, loading 58.3 µmol/g, 1 µmol scale). The oligonucleotide 3'-amino-d($T_{10}$) (27) was synthesized on the support using an ABI Expedite™ Model 8909 DNA/RNA synthesizer with commercial dT-phosphoramidite and commercial synthesis solutions. The synthesis was performed using protocols supplied by the manufacturer of the synthesizer in DMT-OFF mode. A dummy nucleotide was incorporated at the 3'-end of the sequence that was entered into the synthesizer. The oligonucleotide product was cleaved from the supports with 1 ml conc. aqueous ammonia (32%) for 45 minutes at room temperature and further incubated in the ammonia solution at 55° C. Aliquots (150 µl) of the ammonia solution were removed at different time intervals, cooled on ice and dried under vacuum centrifugation. The samples were resuspended in water and analyzed by anion-exchange HPLC on a Dionex DNAPac PA100 column (4×250 mm) eluting with a linear gradient from 10% to 46% B in 22.00 min at 85° C. with a flow rate of 1.5 mL/min, detection at λ=260 nm, buffer A=25 mM Trizma hydrochloride/1 mM EDTA/10% CH$_3$CN, pH 7.5, buffer B=25 mM Trizma hydrochloride/1 mM EDTA/10% CH$_3$CN/1 M NaCl, pH 7.5. The results are set forth in Table 1.

TABLE 1

Deprotection time study for oligonucleotide (27) prepared on support (25) as described in Example 5

| Reaction Time [h] | Rt [min] | Peak Area [%] |
| --- | --- | --- |
| 3 | 14.46 | 74.8 |
| 6 | 14.44 | 87.3 |
| 21 | 14.25 | 87.6 |

Example 6

Investigation of the Time Required for the Complete Deprotection of the Oligonucleotide 3'-Amino-d($T_{10}$) (27) Prepared on Solid Support (26)

Solid support (26) was packed in a standard plastic synthesis columns suitable for ABI Expedite™ Model 8909 DNA/RNA synthesizer (27.8 mg, loading 36.0 µmol/g, 1 µmol scale). The oligonucleotide 3'-amino-d($T_{10}$) (27) was synthesized on the support using an ABI Expedite™ Model 8909 DNA/RNA synthesizer with commercial dT-phosphoramidite and commercial synthesis solutions. The synthesis was performed using protocols supplied by the manufacturer of the synthesizer in DMT-OFF mode. A dummy nucleotide was incorporated at the 3'-end of the sequence that was entered into the synthesizer. The support bound oligonucleotide product was distributed into 5 vials and each portion of the support was treated with 100 µl conc. aqueous ammonia (32%) at 55° C. The incubation times were 1 hour, 2 hours, 4 hours, 6 hours and 24 hours for the different vials. The supports were cooled on ice, centrifuged and the supernatants were individually dried under vacuum centrifugation. The samples were resuspended in water and analyzed by anion-exchange HPLC on a Dionex DNAPac PA100 column (4×250 mm) eluting with a linear gradient from 10% to 46% B in 22.00 min at 85° C. with a flow rate of 1.5 mL/min, detection at λ=260 nm, buffer A=25 mM Trizma hydrochloride/1 mM EDTA/10% CH$_3$CN, pH 7.5, buffer B=25 mM Trizma hydrochloride/1 mM EDTA/10% CH$_3$CN/1 M NaCl, pH 7.5. The results are depicted in FIGS. 2 and 3.

Example 7

Synthesis of the 3'-Amino Oligonucleotide 5'-d (CTC-TCA-GCG-AGC-CTC-AA) (28) on Solid Support (26)

Solid support (26) was packed in a standard plastic synthesis column suitable for ABI Expedite™ Model 8909 DNA/RNA synthesizer (27.8 mg, loading 36.0 µmol/g, 1 µmol scale). The 3'-amino oligonucleotide (28) was synthesized using an ABI Expedite™ Model 8909 DNA/RNA synthesizer with commercial nucleoside phosphoramidites dT, dC(bz), dA(bz) and dG(dmf) (N,N-dimethylformamidine protection) and commercial synthesis solutions. The synthesis was performed using protocols supplied by the manufacturer of the synthesizer in DMT-OFF mode. A dummy nucleotide was incorporated at the 3'-end of the sequence that was entered into the synthesizer. The oligonucleotide product was cleaved from the support with 1 ml conc. aqueous ammonia (32%) for 60 minutes at room temperature and the resulting ammonia solution was further incubated in conc. ammonia at 55° C. for 2 hours. The product was analyzed by anion-exchange HPLC on a Dionex DNAPac PA100 column (4×250 mm) eluting with a linear gradient from 10% to 46% B in 22.00 min at 85° C. with a flow rate of 1.5 mL/min, detection at λ=260 nm, buffer A=25 mM Trizma hydrochloride/1 mM EDTA/10% CH$_3$CN, pH 7.5, buffer B=25 mM Trizma hydrochloride/1 mM EDTA/10% CH$_3$CN/1 M NaCl, pH 7.5. The purity of the prepared oligonucleotide was 80%. The anion exchange chromatogram of oligonucleotide product (28) is depicted in FIG. 4. The product was further characterized by MALDI-TOF mass spectrometry and its identity was confirmed by the observed mass (calcd 5294.5; found 5294.2). 85 OD$_{260}$ were obtained.

Example 8

Simultaneous Synthesis of Oligonucleotides d($T_{15}$) and 3'-Amino d($T_{14}$ as well as Oligonucleotides d($T_{30}$) and 3'-Amino d($T_{29}$) on Mixtures of a Commercial dT-support and Support (26)

A commercial thymidine loaded CPG 500 support (Proligo Biochemie GmbH Hamburg, 36 µmol/g, 14 mg, 0.5 µmol) and solid support (26) (35 µmol/g, 14 mg, 0.49 µmol) were packed together in standard plastic synthesis columns suitable for ABI Expedite™ Model 8909 DNA/RNA synthesizer. The oligonucleotide sequences d($T_{15}$) and dT($T_{30}$) were programmed into the synthesis instrument and the synthesis was performed using protocols supplied by the manufacturer of the instrument in DMT-OFF mode on an ABI Expedite™ Model 8909 DNA/RNA synthesizer with commercial dT-phosphoramidite and commercial synthesis solutions. The oligonucleotide products were cleaved from the supports with conc. aqueous ammonia (32%) for 45 minutes at room temperature and further incubated in conc. ammonia at 55° C. over night. The products from both syntheses were analyzed by anion-exchange HPLC on a Dionex DNAPac PA100 column (4×250 mm). The UV-absorbance of the 2 main oligonucleotide peaks in the chromatograms were recorded and corrected to reflect the presence of 14 and 29, respectively, thymine bases in the 3'-amino oligonucleotides versus 15 and 30, respectively, thymine bases in the non-modified oligonucleotides in order to calculate the molar ratio of the 2 oligonucleotides. The observed molar ratio of the 3'-amino oligonucleotide to the non-modified oligonucleotide was 0.96:1.00 in case of the $d(T_{15})$-sequence and 0.95:1.00 in case of the $d(T_{30})$-sequence. 70 $OD_{260}$ were obtained in case of the $d(T_{15})$-sequence and 211 $OD_{260}$ were obtained in case of the $d(T_{30})$-sequence. The chromatogram for the $d(T_{15})$-sequence is displayed in FIG. 5.

Example 9

Post Synthetic Labeling of the 3'-Amino Oligonucleotide $d(T_{10})$ (27) Synthesized on Solid Support (25) with TAMRA NHS Ester Solid support (25) was packed in a standard plastic synthesis column suitable for ABI Expedite™ Model 8909 DNA/RNA synthesizer (17.1 mg, loading 58.3 µmol/g, 1 µmol scale). The 3'-amino oligonucleotide (27) was synthesized using an ABI Expedite™ Model 8909 DNA/RNA synthesizer with commercial dT-phosphoramidite and commercial synthesis solutions. The synthesis was performed using protocols supplied by the manufacturer of the synthesizer in DMT-OFF mode. A dummy nucleotide was incorporated at the 3'-end of the sequence that was entered into the synthesizer. The oligonucleotide product was cleaved from the support with 1 ml conc. aqueous ammonia (32%) for 45 minutes at room temperature and the resulting ammonia solution was further incubated in conc. ammonia at 55° C. for 6 hours. The resulting solution was cooled on ice and evaporated under vacuum centrifugation. The residue was reconstituted in water (100 µl).

An aliquot (20 µl) of the resulting solution was added to $Na_2CO_3/NaHCO_3$ buffer, pH=9 (480 µl). A 0.17 M solution of TAMRA NHS ester in DMSO (6 µl, 6 equiv., Glen Research, Sterling Va., Cat. No. 50-5910-66) was added to the oligonucleotide and the reaction tube was wrapped in aluminum foil to protect the reaction from light. The mixture was initially vortexed, placed in a heat block at 37° C. and subsequently vortexed every 15 minutes for the first hour. After the first hour, the mixture was left undisturbed in the heat block to incubate at 37° C. overnight. The excess dye was removed from the oligonucleotide solution via gel filtration chromatography using a NAP™-10 gel filtration column containing Sephadex G-25 DNA grade media (Amersham Pharmacia Biotech AB, Uppsala, Sweden, Cat. No. 17-0854-02). The NAP™-10 column was equilibrated with 3 column volumes of water. The oligonucleotide solution was diluted with water to a total volume of 1 ml and loaded onto the NAP™-10 column. The oligonucleotide was eluted from the column by adding an additional volume of water (1.5 ml). The sample was evaporated to dryness and reconstituted in water (150 µl). Both the crude 3'-amino oligonucleotide (27) and the product of the labeling reaction were analyzed by anion-exchange HPLC on a Dionex DNAPac PA100 column (4×250 mm) eluting with a linear gradient from 10% to 46% B in 22.00 min at 85° C. with a flow rate of 1.5 mL/min, detection at λ=260 nm, buffer A=25 mM Trizma hydrochloride/1 mM EDTA/10% $CH_3CN$, pH 7.5, buffer B=25 mM Trizma hydrochloride/1 mM EDTA/10% $CH_3CN$/1 M NaCl, pH 7.5. The purity of the crude 3'-amino oligonucleotide (27) was 86% (retention time 13.2 minutes), the purity of the TAMRA-labeled oligonucleotide product was 69% (retention time 16.8 minutes). Both the crude 3'-amino oligonucleotide (27) and the product of the labeling reaction were further characterized by MALDI-TOF mass spectrometry and their identity was confirmed by the observed mass (calcd for (27) 3159.1; found 3169.6, calcd for the TAMRA labeled oligonucleotide product 3571.6, found 3572.6).

Example 10

Post Synthetic Labeling of 3'-Amino Oligonucleotide $d(T_{10})$ (27) Synthesized on Solid Support (26) with TAMRA NHS Ester Solid support (26) was packed in a standard plastic synthesis column suitable for ABI Expedite™ Model 8909 DNA/RNA synthesizer (27.8 mg, loading 36.0 µmol/g, 1 µmol scale). The 3'-amino oligonucleotide (27) was synthesized using an ABI Expedite™ Model 8909 DNA/RNA synthesizer with commercial dT-phosphoramidite and commercial synthesis solutions. The synthesis was performed using protocols supplied by the manufacturer of the synthesizer in DMT-OFF mode. A dummy nucleotide was incorporated at the 3'-end of the sequence that was entered into the synthesizer. The oligonucleotide product was cleaved from the support with 1 ml conc. aqueous ammonia (32%) for 60 minutes at room temperature and the resulting ammonia solution was further incubated in conc. ammonia at 55° C. for 2 hours. An aliquot of the deprotection solution (200 µl) was cooled on ice and evaporated under vacuum centrifugation.

The dried 3'-amino oligonucleotide (27) was redissolved in $Na_2CO_3/NaHCO_3$ buffer, pH=9 (500 µl). A 0.17 M solution of TAMRA NHS ester in DMSO (6 µl, 6 equiv., Glen Research, Sterling Va., Cat. No. 50-5910-66) was added and the reaction tube was wrapped in aluminum foil to protect the dye from light. The mixture was vortexed, then incubated at 37° C. overnight. The excess dye was removed from the oligonucleotide solution via gel filtration chromatography using a NAP™-10 column, which was equilibrated with water (10 ml). The reaction mixture was loaded onto the column and the oligonucleotide was eluted by adding an additional volume of water (1 ml). The collected oligonucleotide solution was evaporated to dryness, reconstituted in water (150 µl) and analyzed by anion-exchange HPLC on a Dionex DNAPac PA100 column (4×250 mm) eluting with a linear gradient from 10% to 46% B in 22.00 min at 85° C. with a flow rate of 1.5 ml/min, detection at λ=260 nm, buffer A=25 mM Trizma hydrochloride/1 mM EDTA/10% $CH_3CN$, pH 7.5, buffer B=25 mM Trizma hydrochloride/1 mM EDTA/10% $CH_3CN$/1 M NaCl, pH 7.5. The purity of the prepared oligonucleotide was 81%. The product was further characterized by MALDI-TOF mass spectrometry and its identity was confirmed by the observed mass (calcd 3571.6, found 3575.2).

The invention claimed is:

1. A method for the synthesis of 3'-amino oligonucleotides comprising the steps of:
   (a) providing a solid support, wherein said solid support is selected from the group of compounds having the same structure:

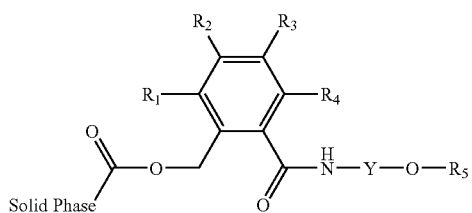

wherein
   R1, R2, R3 and R4 are independent selected from the group consisting of H, alkyl with up to 4 carbon atoms, heteroalkyl with up to 4 carbon atoms, phenyl, alkoxy with up to 4 carbon atoms, heteroalkoxy with up to 4 carbon atoms, carboxy, alkyloxycarbonyl with up to 4 carbon atoms in the alkyl chain, alkylcarbamoyl with up to 4 carbon atoms in the alkyl chain, halo, cyano, nitro, sulfo and alkylsulfonyl with up to 4 carbon atoms in the alkyl chain;
   $R_5$ is H or an acid labile protective group that is removed in the first deblocking step of a solid phase oligonucleotide synthesis; and
   Y is an organic spacer group comprising a straight or branched chain of one or more methylene groups, wherein the chain is optionally interrupted by one or more moieties independently selected from the group consisting of oxygen atoms, carbonyl groups, amide groups, ureido groups, urethane groups and aryl groups;
   (b) synthesizing an oligonucleotide pursuant to standard techniques for solid phase oligonucleotide synthesis (SPOS) wherein the oligonucleotide chain is assembled on the solid support provided in step (a);
   (c) cleaving the oligonucleotide from the solid support, and,
   (d) deprotecting the oligonucleotide compound completely, or deprotecting the oligonucleotide compound completely except for the 5' terminal end protective group.

2. The method of claim 1, wherein the solid phase is a controlled pore glass.

3. The method of claim 1, wherein $R_1$, $R_2$, $R_3$ and $R_4$ are independently selected from the group consisting of H, nitro and halogen.

4. The method of claim 1 wherein Y is —$(CH_2)_n$— or —$CH_2CH_2$—$(OCH_2CH_2)_n$— with n ranging from 1 to 10.

5. The method of claim 1, wherein $R_1$, $R_2$, $R_3$ and $R_4$ are independently selected from the group consisting of H and nitro, Y is —$(CH_2)_n$— with n ranging from 1 to 10, and the solid phase is a controlled pore glass.

6. The method of claim 1, wherein $R_1$, $R_2$, and $R_4$ are H, $R_3$ is H or nitro, Y is —$(CH_2)_6$—, and the solid phase is a controlled pore glass.

7. A method for the synthesis of 3'-amino oligonucleotides comprising the steps of:
   (a) providing a solid support, wherein said solid support is selected from the group of compounds having the following structure:

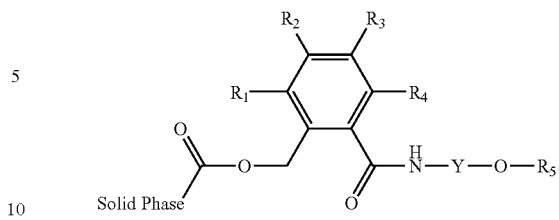

wherein
   wherein $R_1$, $R_2$, $R_3$ and $R_4$ are independently selected from the group consisting of H or an electron withdrawing substituent;
   $R_5$ is H or an acid labile protective group that is removed in the first deblocking step of a solid phase oligonucleotide synthesis; and
   Y is an organic spacer group comprising a straight or branched chain of one or more methylene groups, wherein the chain is optionally interrupted by one or more moieties independently selected from the group consisting of oxygen atoms, carbonyl groups, amide groups, ureido groups, urethane groups and aryl groups;
   (b) synthesizing an oligonucleotide pursuant to standard techniques for solid phase oligonucleotide synthesis (SPOS) wherein the oligonucleotide chain is assembled on the solid support provided in step (a);
   (c) cleaving the oligonucleotide from the solid support, and,
   (d) deprotecting the oligonucleotide compound completely, or deprotecting the oligonucleotide compound completely except for the 5' terminal end protective group.

8. The method of claim 7, wherein $R_1$, $R_2$, $R_3$ and $R_4$ are independently selected from the group consisting of H, nitro and halogen.

9. The method of claim 8, wherein Y is —$(CH_2)_n$— or —$CH_2CH_2$—$(OCH_2CH_2)_n$— with n ranging from 1 to 10.

10. The method of claim 9, wherein $R_1$, $R_2$, $R_3$ and $R_4$ are independently selected from the group consisting of H and nitro, Y is —$(CH_2)_n$— with n ranging from it 1 to 10, and the solid phase is a controlled pore glass.

11. The method of claim 9, wherein $R_1$, $R_2$, and $R_4$ are H, $R_3$ is H or nitro, Y is —$(CH_2)_6$, and the solid phase is a controlled pore glass.

12. A solid support for oligonucleotide synthesis having the following structure:

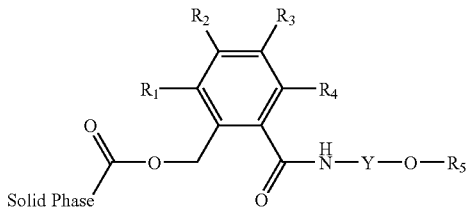

wherein
$R_1$, $R_2$, $R_3$ and $R_4$ are independently selected from the group consisting of H, alkyl with up to 4 carbon atoms, heteroalkyl with up to 4 carbon atoms, phenyl, alkoxy with up to 4 carbon atoms, heteroalkoxy with up to 4 carbon atoms, carboxy, alkyloxycarbonyl with up to carbon atoms in the alkyl chain, alkylcarbamoyl with up to 4 carbon atoms in the alkyl chain, halo, cyano, nitro, sulfo and alkylsulfonyl with up to 4 carbon atoms in the alkyl chain;

$R_5$ is H or an acid labile protective group that is removed in the first deblocking step of a solid phase oligonucleotide synthesis; and Y is an organic spacer group comprising a straight or branched chain of one or more methylene groups, wherein the chain is optionally interrupted by one or more moieties selected from the group consisting of oxygen atoms, carbonyl groups, amide groups, ureido groups, urethane groups and aryl groups.

13. The solid support of claim 12, wherein the solid phase is a controlled pore glass.

14. The solid support of claim 12, wherein $R_1$, $R_2$, $R_3$ and $R_4$ are independently selected from the group consisting of H, nitro and halogen.

15. The solid support of claim 12 wherein Y is —$(CH_2)_n$— or —$CH_2CH_2$—$(OCH_2CH_2)_n$— with n ranging from 1 to 10.

16. The solid support of claim 15, wherein $R_1$, $R_2$, $R_3$ and $R_4$ are independently selected from the group consisting of H and nitro, Y is —$(CH_2)_n$— with n ranging from 1 to 10, and the solid phase is a controlled pore glass.

17. The solid support of claim 15, wherein $R_1$, $R_2$, and $R_4$ are H, $R_3$ is H or nitro, Y is —$(CH_2)6$—, and the solid phase is a controlled pore glass.

18. A solid support for oligonucleotide synthesis having the following structure:

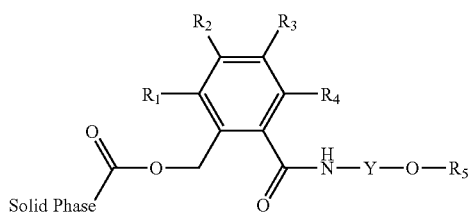

wherein $R_1$, $R_2$, $R_3$ and $R_4$ are independently selected from the group consisting of H or an electron withdrawing group;

$R_5$ is H or an acid labile protective group that is removed in the first deblocking step of a solid phase oligonucleotide synthesis; and Y is an organic spacer group comprising a straight or branched chain of one or more methylene groups, wherein the chain is optionally interrupted by one or more moieties selected from the group consisting of oxygen atoms, carbonyl groups, amide groups, ureido groups, urethane groups and aryl groups.

19. The solid support of claim 18, wherein $R_1$, $R_2$, $R_3$ and $R_4$ are independently selected from the group consisting of H, nitro and halogen.

20. The solid support of claim 19 wherein Y is —$(CH_2)_n$— or —$CH_2CH_2$—$(OCH_2CH_2)_n$— with n ranging from 1 to 10.

21. The solid support of claim 20, wherein $R_1$, $R_2$, $R_3$ and $R_4$ are independently selected from the group consisting of H and nitro, Y is —$(CH_2)_n$— with n ranging from 1 to 10, and the solid phase is a controlled pore glass.

22. The solid support of claim 20, wherein $R_1$, $R_2$ and $R_4$ are H, $R_3$ is H or nitro, Y is —$(CH_2)6$—, and the solid phase is a controlled pore glass.

23. The method of claim 1, wherein step (c) occurs under alkaline conditions.

24. The method of claim 6, wherein $R_5$ is a dimethoxytrityl group.

25. The method of claim 7, wherein step (c) occurs under alkaline conditions.

26. The method of claim 11, wherein $R_5$ is a dimethoxytrityl group.

27. The solid support of claims 17, wherein $R_5$ is a dimethoxytrityl group.

28. The solid support of claims 22, wherein $R_5$ is a dimethoxytrityl group.

* * * * *

SEQUENCE LISTING

<160> NUMBER OF SEQ ID NOS: 4

<210> SEQ ID NO 1
<211> LENGTH: 10
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(10)
<223> OTHER INFORMATION: 3' NH2

<400> SEQUENCE: 1
tttttttttt                                                              10

<210> SEQ ID NO 2
<211> LENGTH: 17
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(17)
<223> OTHER INFORMATION: 3' NH2

<400> SEQUENCE: 2
ctctcagcga gcctcaa                                                      17

<210> SEQ ID NO 3
<211> LENGTH: 14
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(14)
<223> OTHER INFORMATION: 3' NH2

<400> SEQUENCE: 3
tttttttttt tttt                                                         14

<210> SEQ ID NO 4
<211> LENGTH: 15
<212> TYPE: DNA
<213> ORGANISM: Artificial
<220> FEATURE:
<223> OTHER INFORMATION: Synthetic Nucleic Acid Ligand

<400> SEQUENCE: 4
tttttttttt ttttt                                                        15